(12) United States Patent
Koshti

(10) Patent No.: US 9,787,913 B1
(45) Date of Patent: Oct. 10, 2017

(54) METHODS AND SYSTEMS FOR MEASUREMENT AND ESTIMATION OF NORMALIZED CONTRAST IN INFRARED THERMOGRAPHY

(71) Applicant: Ajay M. Koshti, League City, TX (US)

(72) Inventor: Ajay M. Koshti, League City, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 50 days.

(21) Appl. No.: 14/727,383

(22) Filed: Jun. 1, 2015

Related U.S. Application Data

(62) Division of application No. 12/971,919, filed on Dec. 17, 2010, now Pat. No. 9,066,028.

(60) Provisional application No. 61/293,426, filed on Jan. 8, 2010.

(51) Int. Cl.
| | |
|---|---|
| H04N 5/33 | (2006.01) |
| H04N 5/32 | (2006.01) |
| H04N 3/09 | (2006.01) |
| G01B 11/02 | (2006.01) |
| G01J 5/00 | (2006.01) |
| G01J 5/60 | (2006.01) |
| G01N 25/18 | (2006.01) |
| B41M 5/26 | (2006.01) |

(52) U.S. Cl.
CPC ............. *H04N 5/33* (2013.01); *G01B 11/022* (2013.01); *G01J 5/0003* (2013.01); *G01J 5/60* (2013.01); *G01N 25/18* (2013.01); *H04N 3/09* (2013.01); *H04N 5/32* (2013.01); *B41M 5/26* (2013.01)

(58) Field of Classification Search
CPC ... H04N 5/33; H04N 5/32; H04N 3/09; G01B 11/022; G01J 5/0003; G01J 5/60; G01N 25/18; B41M 5/26
USPC ..... 348/164, 162, 135; 250/316.1, 334, 330; 702/135, 134, 136
See application file for complete search history.

(56) References Cited

U.S. PATENT DOCUMENTS

| | | | |
|---|---|---|---|
| 6,013,915 | A | 1/2000 | Watkins |
| 6,054,868 | A | 4/2000 | Borden et al. |
| 6,236,049 | B1 | 5/2001 | Thomas et al. |
| 6,346,704 | B2 | 2/2002 | Kenway |
| 6,367,968 | B1 | 4/2002 | Ringermacher et al. |
| 6,394,646 | B1 | 5/2002 | Ringermacher et al. |

(Continued)

OTHER PUBLICATIONS

Introduction to EchoTherm—Version 6, Thermal Wave Imaging, Inc., 2002, pp. 1-25.

(Continued)

*Primary Examiner* — Shawn An
(74) *Attorney, Agent, or Firm* — Kurt G. Hammerle

(57) ABSTRACT

Methods and systems for converting an image contrast evolution of an object to a temperature contrast evolution and vice versa are disclosed, including methods for assessing an emissivity of the object; calculating an afterglow heat flux evolution; calculating a measurement region of interest temperature change; calculating a reference region of interest temperature change; calculating a reflection temperature change; calculating the image contrast evolution or the temperature contrast evolution; and converting the image contrast evolution to the temperature contrast evolution or vice versa, respectively.

7 Claims, 20 Drawing Sheets

(56) References Cited

U.S. PATENT DOCUMENTS

| | | |
|---|---|---|
| 6,516,084 B2 | 2/2003 | Shepard |
| 6,517,238 B2 | 2/2003 | Sun et al. |
| 6,542,849 B2 | 4/2003 | Sun |
| 6,690,016 B1 | 2/2004 | Watkins et al. |
| 6,712,502 B2 | 3/2004 | Zalameda et al. |
| 6,730,912 B2 | 5/2004 | Sun et al. |
| 6,751,342 B2 | 6/2004 | Shepard |
| 6,838,670 B2 | 1/2005 | Lewis et al. |
| 6,840,666 B2 | 1/2005 | Enachescu et al. |
| 7,149,343 B2 | 12/2006 | Enachescu et al. |
| 7,186,981 B2 | 3/2007 | Shepard et al. |
| 7,220,966 B2 | 5/2007 | Saito et al. |
| 7,365,330 B1 | 4/2008 | Sun |
| 7,419,298 B2 | 9/2008 | Ouyang et al. |
| 7,425,093 B2 | 9/2008 | Wickersham, Jr. et al. |
| 7,457,455 B2 | 11/2008 | Matsui et al. |
| 8,577,120 B1 * | 11/2013 | Koshti ............... G06T 7/0004 250/341.8 |
| 9,066,028 B1 * | 6/2015 | Koshti .................. H04N 5/33 |
| 2003/0137318 A1 | 7/2003 | Enachescu et al. |
| 2004/0125986 A1 | 7/2004 | Larsson et al. |
| 2006/0262971 A1 | 11/2006 | Foes et al. |
| 2009/0237423 A1 | 9/2009 | Shih et al. |

OTHER PUBLICATIONS

Mosaiq Manual Screen Shots from Software Program, Thermal Wave Imaging The Art of Inspection, 2001-2005, pp. 1-13.
ThermoCalc-6L User's Manual, 1998, pp. 1-42.
ThermoHeat-3D User's Manual, 1998, pp. 1-17.

\* cited by examiner

METHODS AND SYSTEMS FOR MEASUREMENT AND ESTIMATION OF NORMALIZED CONTRAST IN INFRARED THERMOGRAPHY

I. CROSS REFERENCE TO RELATED APPLICATIONS

This is a divisional application of application Ser. No. 12/971,919 filed on Dec. 17, 2010, which claims the benefit of U.S. Provisional Application Ser. No. 61/293,426 filed on Jan. 8, 2010.

II. ORIGIN OF THE INVENTION

The invention described herein was made by an employee of the United States Government and may be manufactured and used by or for the Government of the United States of America for governmental purposes without the payment of any royalties thereon or therefor.

III. FIELD OF THE INVENTION

The invention is directed to the fields of non-destructive evaluation (NDE) and of processing of data acquired from an infrared camera. Specifically, the systems and methods described herein concern the performance of a series of steps for analyzing and processing digital data comprising a plurality of infra-red (IR) video images acquired by a system used for non-destructive evaluation.

IV. BACKGROUND OF THE INVENTION

The embodiments described herein relate generally to the field of non-destructive evaluation (NDE) using thermographic images. Infrared (IR) flash (or pulsed) thermography is an example of a technique for NDE used in the inspection of thin materials such as laminated or bonded composites in the aerospace industry. IR flash thermography is used to detect delamination-like anomalies, although other anomalies, such as surface cracks, may be detected.

An example of hardware equipment for an IR flash thermography system comprises a flash lamp (source of light/heat), a flash hood or housing, a flash power supply/trigger unit, a flash duration controller, an IR camera for capturing video images, data acquisition electronics, and a computer. The computer may be used for controlling the flash trigger, for acquiring video data from the IR camera, for displaying data, and for post-processing of the acquired data.

In one example of an NDE technique using IR flash thermography, a single sided or reflection technique is used wherein the flash lamp (heat source) and the IR camera (detector) are on the same side of a test object undergoing inspection. A plate is provided as the test object with a round delamination in the center. After applying heat to the top surface of the test object by triggering the flash lamp, the top surface area surrounding the anomaly cools faster than the top surface (footprint) area above the anomaly. The IR camera captures a sequence of images of the surface temperature in terms of pixel intensity and represents the anomaly as a hot spot e.g., an area warmer than the surrounding area or the reference region of interest (ROI)). The hot spot is about the size and shape of the anomaly footprint. Relative pixel intensity, i.e., the difference in pixel intensity between the hot spot (measurement ROI) and the surrounding area (reference ROI), varies with the post-flash time. Deeper anomalies appear in the IR video data at later times compared to the near surface anomalies. After the initial appearance of an anomaly in the IR video data, the relative pixel intensity continues to increase with time. The relative pixel intensity of the anomaly reaches a peak at a certain time, and then the relative pixel intensity decays until the temperature of the indication area and the temperature of the surrounding area become equal.

V. SUMMARY

In one aspect, disclosed is a method for converting an image contrast evolution of an object to a temperature contrast evolution, the method comprising: calculating a measurement region of interest temperature change $\Delta T$; calculating a reference region of interest temperature change $\Delta T_{ref}$; calculating a reflection temperature change $\Delta T_{refl}$; calculating the image contrast evolution $\bar{C}_W^t$; and converting, using a processor, the image contrast evolution to the temperature contrast evolution.

In another aspect, disclosed is a method for converting a temperature contrast evolution of an object to an image contrast evolution, the method comprising: calculating a measurement region of interest temperature change $\Delta T$; calculating a reference region of interest temperature change $\Delta T_{ref}$; calculating a reflection temperature change $\Delta T_{refl}$; calculating the temperature contrast evolution $\bar{C}^t$; and converting the temperature contrast evolution to the image contrast evolution.

In another aspect, disclosed is an apparatus for converting an image contrast evolution of an object to a temperature contrast evolution, the apparatus comprising one or more processors and one or more memory units coupled to the processors. The apparatus is configured and arranged to calculate a measurement region of interest temperature change $\Delta T$, to calculate a reference region of interest temperature change $\Delta T_{ref}$ to calculate a reflection temperature change $\Delta T_{refl}$, to calculate the image contrast evolution $\bar{C}_W^t$, and to convert the image contrast evolution to the temperature contrast evolution.

In another aspect, disclosed is an apparatus for converting a temperature contrast evolution of an object to an image contrast evolution, the apparatus comprising one or more processors and one or more memory units coupled to the processors. The apparatus is configured to: calculate a measurement region of interest temperature change $\Delta T$; calculate a reference region of interest temperature change $\Delta T_{ref}$, calculate a reflection temperature change $\Delta T_{refl}$, calculate the temperature contrast evolution $\bar{C}^t$; and convert the temperature contrast evolution to the image contrast evolution.

In another aspect, disclosed is a method for assessing emissivity of an object being inspected by an infrared flash thermography system, the method comprising the steps of: measuring a pre-flash temperature at a measurement region of interest $W^0$; calculating a camera constant $C_{cam}$; and calculating the emissivity of the object according to the equation of:

$$\varepsilon \cong \frac{\frac{W^0}{B} - J}{1 - J}.$$

In yet another aspect, disclosed is a method for calculating an afterglow heat flux evolution the method comprising the steps of measuring a reflection temperature $T_{refl}$, and calculating the afterglow heat flux evolution $S_{postflash}$ according to the equation of:

$$S_{postflash} = \sigma(T_{refl}^4 - T_{refl^0}^4),$$

wherein $T_{refl}^0$ is the reflection temperature at time of flash and $\sigma$ is the Stefan-Boltzmann Constant.

VI. BRIEF DESCRIPTION OF THE DRAWINGS

FIG. 1 is a schematic diagram of an exemplary single-sided flash thermography system in accordance with some embodiments described herein.

FIGS. 2(a) and (b) are a schematic diagram of a plate depicting a gapping delamination with measurement and reference regions of interest (ROIs) and a single infrared (IR) video image of a test object with back drilled flat bottom holes, respectively, in accordance with some embodiments described herein.

Figure 1:
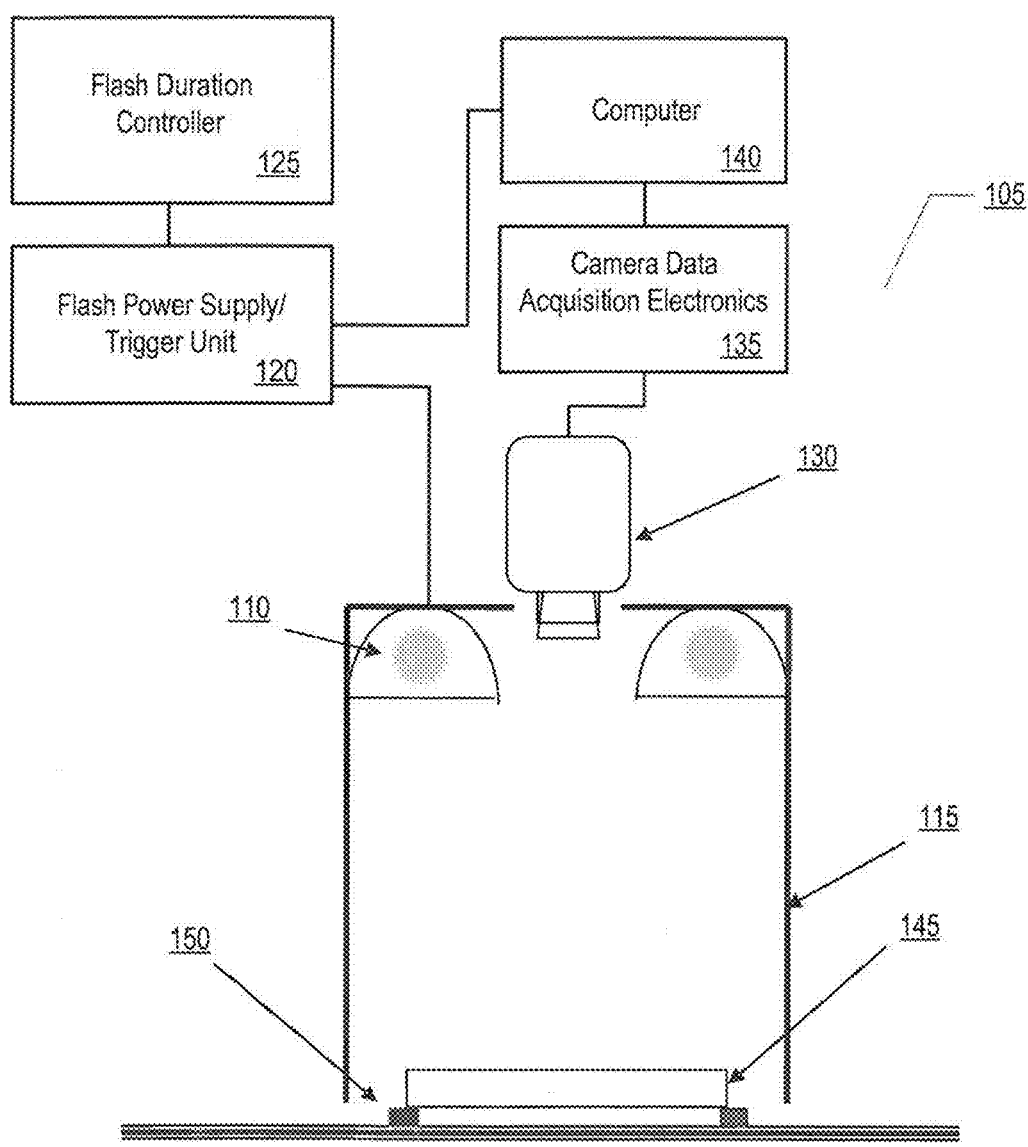

Because the embodiments described herein are subject to various modifications and alternative forms, it should be understood that the drawings and detailed description are not intended to limit the invention to the particular embodiments described herein. Instead, the following description is intended to cover all modifications, alternatives, and equivalents falling within the scope of the invention as defined by the appended claims.

VII. DETAILED DESCRIPTION

The objects in the drawings are not necessarily to scale and certain features may be shown exaggerated in scale or in somewhat generalized or schematic form in the interest of clarity and conciseness. In the description which follows like parts may be identified throughout the specification and drawings with the same reference numerals. The foregoing brief description of the drawings is provided for a more complete understanding thereof. It should be understood, however, that the embodiments described herein are not limited to the precise arrangements and configurations shown. Although the design and use of various embodiments are discussed in detail below, it should be appreciated that the embodiments described represent concepts that may be embodied in a wide variety of contexts. The specific aspects and embodiments described herein are merely illustrative, for it would be impossible or impractical to include all of the possible embodiments and contexts in this description of the invention. Upon reading this description, alternative embodiments will be apparent to persons of ordinary skill in the art.

During the processing of digital data acquired from an infrared camera, normalized image (or pixel intensity) contrast and normalized temperature contrast differ in value for objects having a value of emissivity other than one. Therefore, for more accurate processing of data obtained from objects having an emissivity value other than one, the two quantities should not be treated as the same. In the co-pending U.S. patent application Ser. No. 12/900,644, filed Oct. 8, 2010 and entitled "Methods and Systems for Characterization of an Anomaly Using Infrared Flash Thermography", which is hereby incorporated in its entirety by reference, Koshti distinguishes and defines the two quantities of normalized pixel intensity contrast and normalized temperature contrast. Embodiments described herein establish formulas to estimate the normalized temperature contrast from the normalized pixel intensity or image contrast using the methods and systems described herein. The method includes steps for the measurement of the reflection temperature evolution by comparing the simulation temperature contrast with the measured pixel intensity contrast. The method also comprises the act of estimating the incident heat flux. Ideally, the simulation should model the compound heat source flux evolution which also includes the thermal afterglow. The effect of the reflection temperature in the pixel intensity should also be accounted for to seek a more refined estimation of the temperature contrast profile from the pixel intensity evolution data.

The method of measuring reflection temperature evolution is described herein. First, the reflection temperature evolution is established based on infrared (IR) flash thermography (or simply any transient thermography) data acquisition. This acquisition of data requires a test object, a high emissivity tape with known emissivity, and a diffused but highly reflective metal foil with known reflectivity. The method also records the steady state pre-flash temperature of the object using a thermocouple (or other contact sensor) or an accurate radiometer. The IR datacube is recorded after performing the technique of IR flash thermography.

The method further comprises data acquisition from four regions of interests (ROI). One region is for the measurement area. The second ROI is for the reference area. The third ROI is for the measurement of the reflection temperature. The fourth ROI is for the measurement of the pre-flash temperature of the high emissivity tape.

Using formulas given herein, the method estimates the reflection temperature evolution, Then, the method computes the temperature contrast from the IR data. The emissivity factor is defined to relate the temperature contrast to the image contrast.

The method uses the reflection temperature evolution to model the afterglow flux of the flash source. Using the estimated compound source evolution in the simulation software, the method can estimate the temperature contrast evolutions and then estimate the image contrast profiles on simulated voids.

The invention provides an emissivity estimation technique using the same IR camera. The technique estimates the emissivity of an object for a desired thermal wavelength. It is shown that using the foil-tape (or tape-foil) technique during the IR shot, the transient reflection temperature or the reflection temperature evolution can be recorded. If the IR camera is programmed to use the real-time reflection temperature using the formulas described herein, it can provide real-time object surface temperature. The IR camera can be programmed to estimate the object emissivity in real-time using the formulas derived herein for the foil-tape technique.

Referring now to the drawings, FIG. 1 is a schematic diagram of an exemplary single-sided flash thermogaphy system in accordance with some embodiments described herein. As shown in FIG. 1, the equipment for an infrared (IR) flash thermography (IRFT) system 105 in accordance with at least one of the exemplary embodiments described herein comprises a flash lamp (source of light/heat) 110, a flash-hood 115, at least one flash power supply/trigger unit. 120, at least one flash duration controller 125, an IR camera 130 for capturing video images, camera data acquisition electronics 135, and a computer 140. The computer 140 is used for controlling the flash trigger unit 120 for powering the flash lamp 110, data acquisition of the camera video data, data display, and post processing of the acquired data. The flash-hood 115 may be made from sheet metal and have highly reflective ($\epsilon$=0.05) inside wall surfaces. The flash-hood may form a box-like structure, although other structures that form an interior volume, such as a cylinder, hemi-sphere, etc. may also be used. However the flash-hood is structurally configured, one portion of the hood has a large opening so as to enable the hood to be positioned over a test object 145. The side opposite to the opening has a hole in the center to provide a window for the lens of the IR camera 130 that is positioned outside of the flash-hood 115. The IR camera 130 is focused at a surface of the test object 145 positioned within the hood. At least one flash lamp 110 (two are shown in FIG. 1) is located within the inner wall of the flash-hood 115 in proximity to the IR camera 130. The flash lamp(s) 110 is covered with a glass shield which is highly transmissive for light but highly emissive for thermal radiation. The flash lamp(s) 110 when powered directs illumination towards the test object 145 without directly shining light upon or into the IR camera 130. The flash-hood 115 functions as a housing that contains most of the intense flash from the flash lamp 110.

If the size of the test object 145 can be accommodated inside the hood 115, then the test object 145 is located at the hood opening or slightly inside the hood 115. Otherwise, the test object 145 is located slightly outside of the hood 115 opening. A short duration (e.g. 3 millisecond), intense (12 kJ) flash is triggered by the computer 140. Data acquisition is initiated a few seconds before the flash, and it continues until a prescribed duration of time has expired. The camera 130 provides a sequence of IR images (or frames) called the data-cube (or digital video) of the test object surface taken at the chosen frame rate (e.g. 60 Hz or 60 frames per see). As described in further detail herein, the intensity (numerical value) of each pixel of the image is a function of the surface temperature of the corresponding area observed of the test object 145 at the time of the image frame. The flash causes the surface of the test object 145 to warm up slightly, and the heat then starts to dissipate rapidly. The surface cools through thermal radiation, convection, and conduction. Heat conduction within the test object 145 is considered to be the dominant heat transfer mode until the temperature gradients within the test object become small. At later times, the heat conduction is of the order of the combined effect of heat convection and radiation. The IR data acquisition and data analysis utilizes the thermal data in the short duration immediately after the flash where the thermal dissipation is dominated by the heat conduction within the test object 145.

Heat exchange across the boundaries due to convection can be assumed to be zero if the Biot number ($N_{Bi}$=hL/k) is less than 0.1. For example, a half centimeter thick graphite/epoxy (k=0.64 W/mK) plate, using h=10 W/m$^2$K, has a Biot number of 0.078. Therefore, heat conduction is the dominant mode of heat transfer in this graphite/epoxy plate example. Thinner test objects tend to equalize the temperature within the test object very quickly and have a relatively longer cooling time by heat loss to environment.

Figure 2A:
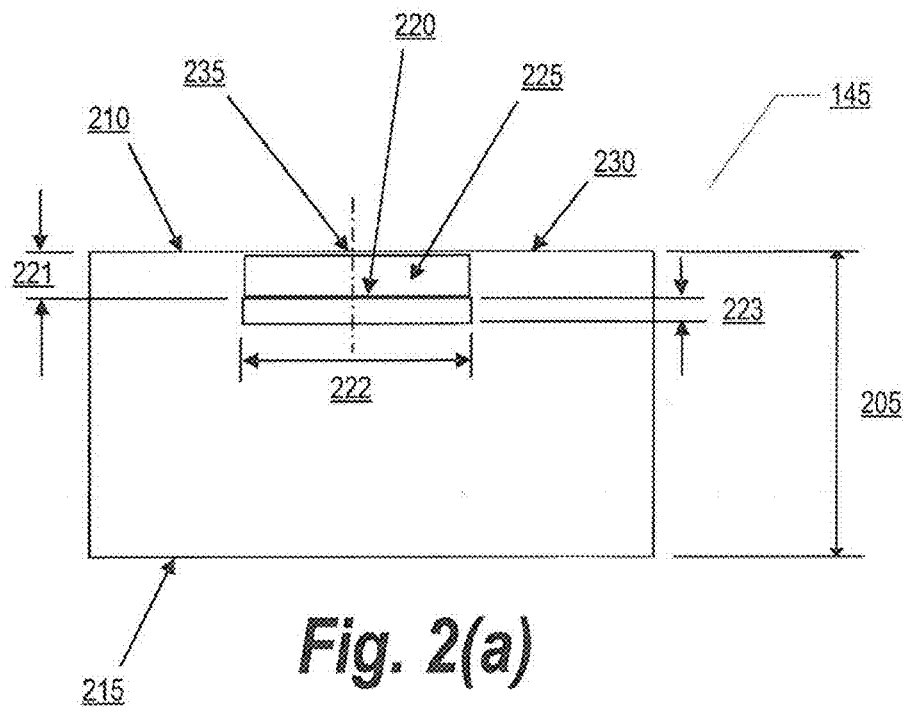
Figure 2B:
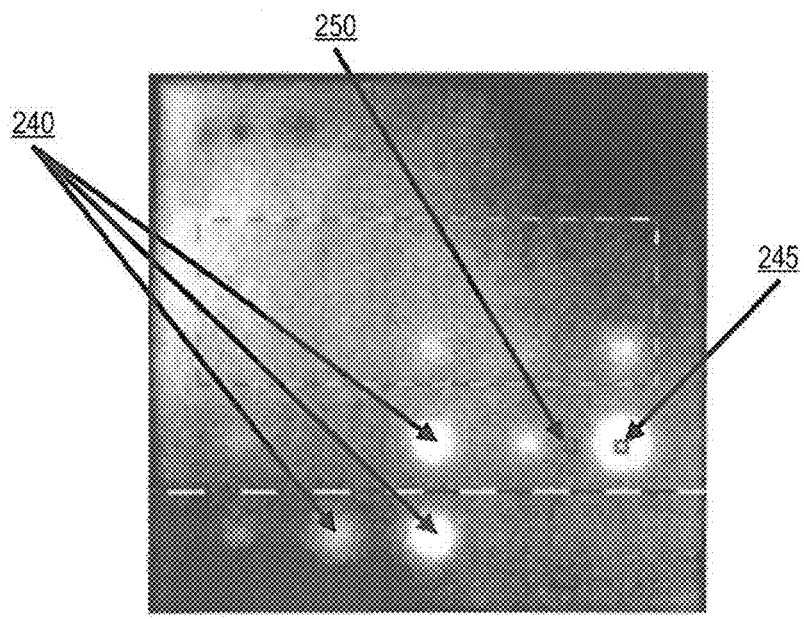

FIG. 2(a) is a schematic diagram of a plate serving as the test object 145. FIG. 2(a) depicts a gapping delamination or anomaly 220 with measurement and reference regions of interest (ROIs) in accordance with embodiments described herein. FIG. 2(b) shows a single infrared (IR) video image of a test object with a flat bottom hole in accordance with at least one embodiment. Referring now to FIGS. 1 and 2(a), the test object 145 is made of a thermally isotropic material with constant thickness 205 that fits inside the hood 115. The test object 145 is supported at the corners on insulating standoffs 150 and the hood is oriented vertically thereabove. Assuming that the flash intensity is uniform over the test object top surface 210, the heat conduction will be in a direction normal to the test object top surface 210 in most of the acreage area (i.e., area away from edges of the test object and flash boundary). The heat is conducted uniformly from the top surface of the test object 210 to the bottom surface of the test object 215. Normal heat conduction will be obstructed by an anomaly such as a small round gapping delamination 220 at the center of the test object, as depicted in FIG. 2(*a*). The delamination 220 is at some depth (d) 221 below the top surface of the test object 210. The delamination may also be characterized as having sonic diameter (D) or width 222 and a gap 223. The volume bounded by the anomaly 220 on one side and the top surface 210 on the other side is called the heat trapping volume 225.

The top surface area 230 surrounding the anomaly 220 cools faster than the top surface (footprint) area 235 above the anomaly 220. The IR camera 130 captures the surface temperature image in terms of the pixel intensity and shows the anomaly 220 as a hot spot (e.g. an area warmer than the surrounding area) which is about the size and shape of the anomaly footprint. The relative pixel intensity of the hot spot changes with the time. Deeper anomalies appear at later times in the IR video compared to the near surface anomalies. After the appearance of an anomaly in the IR video, its relative pixel intensity continues to increase with time. The relative pixel intensity associated with the anomaly reaches a peak at a certain time, and then the relative intensity decays until the indication area temperature and the surrounding area temperature become equal.

FIG. 2(*b*) shows one of the frames in a sample IR data-cube from a reinforced carbon-carbon (RCC) part with round flat bottom holes (FBHs) machined into the back surface to simulate gapping delaminations of differing depths. IR indications 240 from different flat bottom holes are clearly visible in the IR image. A measurement ROI 245 is shown as a square in the middle of one of the anomalies. A reference ROI 250 is shown as a square outside the anomaly area. As the test concludes, the test object continues to cool down to ambient temperature through heat convection and radiation.

In some embodiments, such as for a test object that is a flat plate with a large diameter, the top surface may be represented as being at a temperature $T_1$ and similarly the bottom surface is at a temperature $T_2$. A heat conduction rate for an isotropic slab may accordingly be given by equations (1) and (2), $$q_k = \frac{T_1 - T_2}{(L/kA)} \text{ and} \tag{1}$$

$$R_k = \frac{L}{kA}, \tag{2}$$

where $q_k$ is the heat conduction rate (cal-sec$^{-1}$ or BTU-hr$^{-1}$), k is the thermal conductivity (cal-sec$^{-1}$-° C.$^{-1}$-cm$^{-1}$ or BTU-hr$^{-1}$-° F.$^{-1}$-ft$^{-1}$), A is the cross sectional area of the plate (cm$^2$ or ft$^2$), L is the thickness of the plate (cm or ft), and $R_k$ is the conductive resistance (sec-cal$^{-1}$-° C. or hr-BTU$^{-1}$-° F.). Equations (1) and (2) may be used for representing heat conduction across a delamination gap L with one surface at temperature $T_1$ and the other at temperature $T_2$.

In some embodiments, such as for a flat plate with a large diameter, the heat convection rate from a surface is given by equations (3) and (4), $$q_h = \frac{T_{surf} - T_{amb}}{(1/h_{conv}A)} \text{ and} \tag{3}$$

$$R_h = \frac{1}{h_{conv}A}, \tag{4}$$

where $T_{surf}$ is the top surface temperature, $T_{amb}$ is the ambient temperature of the air contacting the surface, $q_h$ is the heat convection rate (cal-sec$^{-1}$ or BTU-hr$^{-1}$), $h_{conv}$ is the heat convection film coefficient (cal-sec$^{-1}$-° C.$^{-1}$-cm$^{-2}$, BTU-hr$^{-1}$ F.$^{-1}$-ft$^{-2}$ or W-K$^{-1}$-m$^{-2}$), A is the surface area of the plate (cm$^2$, m$^2$ or ft$^2$), and $R_h$ is the convective resistance (sec-cal$^{-1}$-° C. or hr-BTU$^{-1}$-° F.). For natural (unforced) convection, a typical value for the heat convection film coefficient is 4 W-K$^{-1}$-m$^{-2}$. Using equations (3) and (4), the heat convection rate across each side of a delamination air gap with one surface at temperature $T_1$ and other surface at temperature $T_2$ ($T_1 > T_2$) is given by equation (5a), $$q_h = \frac{T_1 - T_{amb}}{(1/h_{conv}A)} = \frac{T_{amb} - T_2}{(1/h_{conv}A)} \tag{5a}$$

Further, the ambient temperature of the air for thin gaps is given by equation (5b), $$T_{amb} = \frac{T_1 + T_2}{2} \tag{5b}$$

When the air gap becomes smaller than a threshold value represented as the Biot number, the amount of heat exchange by convection is replaced by heat conduction. The heat exchange across the boundaries due to the convection can be assumed to be zero if the Biot number is less than or equal to 0.1 ($N_{Bi}$=hL/k≤0.1). This relationship gives an expression for the threshold air gap thickness as $L_{thr}$=0.1 k/h. Taking the air conductivity to be 0.026 W/mK and assuming the convection coefficient to be 5 W/m$^2$K, then a threshold gap thickness of 0.020 inch (0.5 mm) is calculated, beyond which heat convection is applicable. Heat conduction is present if the gap thickness is less than the threshold gap thickness. The narrowing of the air gap results in increased heat conduction across the air gap, which manifests as a decrease in the peak contrast value of the void. Loss of the peak contrast value by 20% may not occur until the gap narrows significantly compared to the threshold value of the gap thickness.

In some embodiments, such as for a flat plate with a large diameter, the radiative heat transfer rate is given by equations (6), (7), and (8), $$q_r = \frac{T_{surf} - T_{refl}}{(1/h_rA)}, \tag{6}$$

$$h_r = \epsilon\sigma(T_{surf} + T_{refl})(T_{surf}^2 + T_{refl}^2), \text{ and} \quad (7)$$

$$R_r = \frac{1}{h_r A}, \quad (8)$$

where $T_{refl}$ is the apparent temperature experienced by the object surface due to the camera-side background temperature in units of Kelvin or Rankine, $T_{amb}$ is the temperature of the air surrounding the object in Kelvin or Rankine, $\sigma$ is the Stefan-Boltzmann. Constant $5.670400 \times 10^{-8}$ W·m$^{-2}$·K$^{-4}$, $\epsilon$ is the emissivity of the test object surface (assuming same emissivity on top (front) and bottom (rear) surfaces), $h_r$ is the heat radiation transfer coefficient (cal-sec$^{-1}$-° C.$^{-1}$-cm$^{-2}$ or BTU-hr$^{-1}$-° F.$^{-1}$-ft$^{-2}$), and $R_r$ is the radiative resistance (sec-cal$^{-1}$-° C. or hr-BTU$^{-1}$-° F.). At a temperature of 300 K for a 10 K temperature difference between the object surface temperature and the corresponding reflection (background) temperature, the radiation transfer coefficient is less than 6 W-K$^{-1}$-m$^{-2}$.

In some embodiments, such as for a large but thin slab of isotropic material with uniform thickness that is exposed to a heat pulse on the front surface, the resulting one dimensional transient heat transfer is described by equations (9) and (10a), $$\frac{dT}{dt} = \alpha \cdot \frac{d^2 T}{dz^2} \text{ and} \quad (9)$$

$$T(t=0) = T_{in}, \quad (10a)$$

where $\alpha$ is the test object (slab) diffusivity (cm$^2$/s), and z is the distance along the thickness direction. The total heat transfer rate at the slab surface is given by equation (10b), $$q = q_k + q_h + q_r. \quad (10b)$$

Neglecting the air emission, the heat flux boundary conditions are given by, equations (11) and (12), $$-\left(k \cdot \frac{dT}{dz}\right)_{front} = q - h_{front}(T_{front} - T_{amb-front}) - \sigma\epsilon(T_{front}^4 - T_{refl-front}^4) \quad (11)$$

$$-\left(k \cdot \frac{dT}{dz}\right)_{rear} = q - h_{rear}(T_{rear} - T_{amb-rear}) - \sigma\epsilon(T_{rear}^4 - T_{refl-rear}^4), \quad (12)$$

where $T(t=0) = T_{in}$ is the initial steady state temperature of the test object before the flash and $h_{front}$ and $h_{rear}$ are the convection coefficients at the front and rear surfaces, respectively.

In practice, an IR camera measures pixel intensity. Radiometric cameras can measure the surface temperature. Radiometric cameras are not known to be set-up for compensating the transient surrounding temperature. Radiometric cameras may have input for a constant reflection (background) temperature. They may use a reflective foil to assess the stable reflection temperature. For the exemplary embodiments described herein, either a radiometric IR camera (i.e. measure apparent temperature) or an IR camera that measures the irradiance (i.e. measure pixel intensity) may be used because the exemplary embodiments use a method described herein to capture the transient reflection temperature. The method assumes that camera pixel intensity response is proportional to the camera irradiance in the desired temperature range.

Considering the definition of the normalized contrast based on the pixel intensity, its relationship with the temperature of the test object will be derived. The pixel refers to the camera image picture element. The pixel size refers to the instantaneous field of view (IFOV), which is the corresponding area of the object surface imaged in the pixel. A selected pixel grid area, usually in the form of a rectangle, is called the image region of interest (ROI, or when plural ROIs). The size of the ROI then refers to the area of the object surface imaged in the ROI. The corresponding area of the test object is referred to as the object ROI. The camera measures total radiation incident on its detector array element and displays it as a pixel in the image. The detector element response or the pixel intensity registered by the camera is governed by the following equation (13a), $$W = W_{obj} + W_{refl} + W_{atm}, \quad (13a)$$

where W is the average pixel intensity due to the heat irradiance (measured in units of W/m$^2$, cal-sec$^{-1}$-cm$^{-2}$, or BTU-hr$^{-1}$-ft$^{-2}$) of the corresponding camera detector elements from the object ROI measured in gray scale bit value (positive integers). The right hand terms in equation (13a) are given by equations (14), (15), and (16), $$W_{obj} = \epsilon\tau W'_{obj}, \quad (14)$$

$$W_{refl} = (1-\epsilon)\tau W'_{refl}, \text{ and} \quad (15)$$

$$W_{atm} = (1-\tau)\tau W'_{atm}, \quad (16)$$

where $W_{obj}$ is the contribution to the pixel intensity due to the heat emission from the object ROI, $W_{refl}$ is the contribution to the pixel intensity due to the heat reflection from the object ROI, and $W_{atm}$ is the contribution to the pixel intensity due to the heat emission from the air between the object ROI and camera. If the method assumes a perfect focus and that the ROI has a uniform temperature at any time, then equations (17), (18), and (19) will apply, $$W'_{obj} = C_{cam}\sigma T^4, \quad (17)$$

$$W'_{refl} = C_{cam}\sigma T_{refl}^4, \text{ and} \quad (18)$$

$$W'_{atm} = C_{cam}\sigma T_{atm}^4, \quad (19)$$

where W'$_{obj}$ is the uncompensated contribution to the pixel intensity due to the heat emission from the test object ROI, W'$_{refl}$ is the uncompensated contribution to the pixel intensity due to the heat reflection from the test object ROI, W'$_{atm}$ is the uncompensated contribution to the pixel intensity due to the heat emission from the air between the camera and object, T is the surface temperature in Kelvin or Rankine, $T_{refl}$ is the apparent temperature experienced by the object surface due to the camera-side background temperature in Kelvin or Rankine, $T_{atm}$ is the temperature of the air between the camera and the object in Kelvin or Rankine, $C_{cam}$ is the camera constant, $\epsilon$ is the thermal emissivity of the test object surface, and $\tau$ is the thermal radiation (at camera detection wavelength) transmissivity of the air between the test object and the camera. The thermal emissivity is dependent on the thermal wavelength for a non-gray body. The wavelength spectrum is affected by the surface temperature. Assuming that the emissivity is high and the test object is a gray body, the emissivity is not dependent on the wavelength. However, the IR camera measures radiation in a selected band of the wavelength (e.g. 3-5 micron). Equations (17), (18), and (19)

apply to the total radiation integrated over all wavelengths. Thus, in reality, in equations (17), (18), and (19), the exponent (or power) of the temperature variable T may not be equal to four. The exponent of the temperature variable may be between 2 to 17. The following analysis is applicable for these values of the exponent.

A calibrated camera provides a linear response with the thermal radiation incident on the detector array element. This relationship implies that, in a hypothetical case of absolute zero temperature, if the camera calibration is extrapolated, all detector elements shall provide zero pixel intensity. The method assumes that the camera constant is the same within a range of 280 K to 350 K. The pixel intensity or the pixel grayscale value also depends upon the pixel bit resolution (typically 14 bit). The pixel intensity has an upper saturation limit dictated by the pixel bit resolution. A typical InSb mid-wave camera used in flash thermography operates at a wavelength of about 3 to about 5 micron. The transmissivity of air is a function of the distance, humidity, air composition, and wavelength. A pronounced dip in the transmissivity occurs at a wavelength of 4.2 micron due to $CO_2$ absorption. Due to a short distance (~1 ft) between the camera and the test object, the contribution of air emission (emissivity~0) is very small and is neglected herein. Correspondingly, the air transmission (transmissivity~1) is almost 100%. The microbolometer long-wave camera works in the 9 to 12 micron wavelength and has better air transmissivity even for longer distances of several feet (e.g. 30 ft). Therefore, equation (13a) can be simplified to equation (13b), $$W \cong W_{obj} + W_{refl}. \tag{13b}$$

The normalized image contrast is defined based on the pixel intensity as expressed in equations (20), (21), and (22), $$\overline{C}_W^t = \frac{\Delta W - \Delta W_{ref}}{\Delta W + \Delta W_{ref}}, \tag{20}$$

$$\Delta W = W - W^0, \text{ and} \tag{21}$$

$$\Delta W_{ref} = W_{ref} - W_{ref}^0, \tag{22}$$

where $\overline{C}_W^t$ is the normalized IR image (pixel intensity) contrast, $\Delta W$ is the change in the pixel intensity of the measurement ROI after the flash, W is the pixel intensity at the measurement ROI at the post-flash time t, $W^0$ is the pixel intensity at the measurement ROI before the flash, $\Delta W_{ref}$ is the change in the pixel intensity of the reference ROI after the flash, $W_{ref}$ is the pixel intensity at the reference ROI at the post-flash time t, and $W_{ref}^0$ is the pixel intensity at the reference ROI before the flash. The normalized image contrast is also called the normalized irradiance or pixel intensity contrast.

The normalized surface temperature contrast is defined as expressed in equations (23), (24), and (25), $$\overline{C}^t = \frac{\Delta T - \Delta T_{ref}}{\Delta T + \Delta T_{ref}}, \tag{23}$$

$$\Delta T_{ref} = T_{ref} - T_{ref}^0, \text{ and} \tag{24}$$

$$\Delta T = T - T^0, \tag{25}$$

where $\overline{C}^t$ is the normalized flash surface temperature contrast, $\Delta T$ is the change in the surface temperature of the measurement ROI after the flash, T is the surface temperature at the measurement ROI at the post-flash time t, $T^0$ is the surface temperature at the measurement ROI before the flash, $\Delta T_{ref}$ the change in the surface temperature of the reference ROI after the flash, $T_{ref}$ is the surface temperature at the reference ROI at the post-flash time t, and $T_{ref}^0$ is the surface temperature at the reference ROI before the flash.

The normalized image contrast is related to the normalized temperature contrast. As a first approximation, an exemplary embodiment of the methods described herein assumes that the air transmissivity is unity due to short distance (e.g. 1 ft) and the air heat radiation is negligible between the object and the camera. Therefore, equation (13a) simplifies to equation (26), $$W \cong \epsilon W'_{obj} + (1-\epsilon)W'_{refl}. \tag{26}$$

Substituting equations (17) and (18) into equation (26) results in equation (27), $$W \cong C_{cam}\sigma(\epsilon T^4 + (1-\epsilon)T_{refl}^4). \tag{27}$$

Assuming that the contribution to the pixel intensity from the reflected temperature remains the same between the measurement ROI and the reference ROI, the temperature rise at the measurement (object) ROI is related to the rise in the pixel intensity at the corresponding image ROI by equations (28) and (29), $$\Delta W \cong C_{cam}\sigma(\epsilon(T^4 - T^{0^4}) + (1-\epsilon)(T_{refl}^4 - T_{refl}^{0^4})), \text{ and} \tag{28}$$

$$\Delta W_{ref} \cong C_{cam}\sigma(\epsilon(T_{ref}^4 - T_{ref}^{0^4}) + (1-\epsilon)(T_{refl}^4 - T_{refl}^{0^4})). \tag{29}$$

Substituting the equations (28) and (29) in the definition of image contrast, equation (20), the method arrives at the expression in equation (30), $$\overline{C}_W^t \cong \frac{\varepsilon\left((T^4 - T^{0^4}) - (T_{ref}^4 - T_{ref}^{0^4})\right)}{\left(\varepsilon\left((T^4 - T^{0^4}) + (T_{ref}^4 - T_{ref}^{0^4})\right) + 2(1-\varepsilon)(T_{refl}^4 - T_{refl}^{0^4})\right)}. \tag{30}$$

If a simulation program, such as the software program sold commercially known as ThermoCalc, is used to generate the temperature evolution at the measurement and reference ROIs, then equation (30) can be used to generate the image contrast evolution provided the method estimates the reflection temperature evolution. In practice, the reflection temperature changes with time due to cooling of the flash lamps. The reflected temperature evolution can be estimated based on the measured data on a high reflectivity foil and a high emissivity tape. With the estimation of the reflected temperature evolution, the expression of equation (30) can be used to estimate the normalized image contrast.

The estimated image contrast would be partially compensated for the reflection temperature. Only the camera measurement for the reflection temperature is compensated. The reflection temperature evolution is a measure of the heat source (or incident) temperature evolution. The net heat transfer due to the radiation is relatively small. Heat convection is accounted for in the simulation performed by the ThermoCalc software. The simulation program provides choices for the shape and duration of the heat pulse. Depending upon the user's choice, the heat source simulation may or may not model the afterglow or the reflection temperature. Thus, if the reflection temperature is not modeled in the simulation, then the estimation of the image contrast from the simulated temperature would be considered to be partially compensated for the afterglow.

Alternatively, a second approach is to increase the convective heat transfer coefficient by the average radiation heat transfer coefficient. The convective heat transfer coefficient is of the order of 5 W/m$^2$K for flash thermography. Although, the radiative heat transfer coefficient is a function of the temperature, it is less than 5 W/m$^2$K for a 10 K difference in the temperature range of about 300 K ambient temperature. The radiative heat transfer coefficient can be lumped together with the convective heat transfer coefficient to a value of 10 W/m$^2$K in the simulation. This relationship may allow better prediction of the surface temperature in the flash thermography using the model and also better prediction of the image contrast.

Yet another approach is to model the heat source as a high intensity pulse followed by a very low intensity decaying afterglow.

The estimation of the temperature contrast from the IR measurement requires measurement of the pre-flash surface temperature and the measurement of pixel intensity of a black tape affixed to the surface of the test object. For instance, the method may use a high emissivity ($\epsilon$>0.95) tape (e.g., tape sold commercially by the 3M Company under the product name of 3M 33 or 3M Scotch Brand 235) positioned near the test object. The emissivity of the tape is assumed to be constant for both the pre-flash and the post-flash times. The method measures the pre-flash surface temperature of an ROI in the center of the black tape using a calibrated radiometric IR camera. The surface temperature needs to be close to the equilibrium or steady state. The method also measures the ROI intensity and assumes a high transmissivity value for the air. Thus the pixel intensity due to the tape can be expressed as given in equation (31), $$W_{tape} = C_{cam} \sigma ((1-\epsilon_{tape})T_{refl}^4 + \epsilon_{tape} T_{tape}^4). \tag{31}$$

Due to the high emissivity of the tape, equation (31) can be simplified to equation (32), $$W_{tape} \cong C_{cam} \sigma (\epsilon_{tape} T_{tape}^4). \tag{32}$$

If the method measures the pre-flash tape temperature, then the method can estimate the camera constant ($C'_{cam}$) as given in the expression of equation (33), $$C'_{cam} = C_{cam}\sigma \cong \frac{W_{tape}^0}{\epsilon_{tape} T_{tape}^{04}}. \tag{33}$$

Later a more precise expression for the camera constant will be derived.

To measure the $T_{refl}$ or $W_{refl}$, the method introduces a diffused high reflectivity ($\epsilon$<0.05) reflector such as an aluminum foil that is adequately wrinkled. The emissivity of the foil is assumed to be constant for both pre-flash and post-flash times. The foil is placed level with the object and close to the physical location of the measurement and reference ROIs, such as on the top surface of the test object surface. The method can use two foils, one on either side of the measurement ROI. Here, the method assumes that the reflection temperature is uniform over the test object and the foil, as given by equation (34), $$W_{foil} = C_{cam}\sigma((1-\epsilon_{foil})T_{refl}^4 + \epsilon_{foil} T_{foil}^4). \tag{34}$$

The contribution of the foil emission is relatively small compared to the foil reflection. In the exemplary method, from equation (34), an expression for the reflection temperature may be written as expressed in equation (35), $$T_{refl}^4 \cong \frac{W_{foil} - W_{tape}^0 \left(\frac{\epsilon_{foil}}{\epsilon_{tape}}\right)\left(\frac{T_{foil}^4}{T_{tape}^{04}}\right)}{C'_{cam}(1-\epsilon_{foil})}. \tag{35}$$

Also, the exemplary method assumes that the foil temperature is about same as the pre-flash reference temperature due to the contact with the test object. The black tape is in contact with the test object, therefore the temperature estimations of equation (36) hold $$T_{foil} \cong T_{foil}^0 \cong T_{ref}^0 \cong T_{tape}^0. \tag{36}$$

Equation (35) then simplifies to equation (37a), $$T_{refl}^4 \cong \frac{W_{foil} - W_{tape}^0 \left(\frac{\epsilon_{foil}}{\epsilon_{tape}}\right)}{C'_{cam}(1-\epsilon_{foil})}. \tag{37a}$$

The pre-flash reflection temperature may then be expressed by equation (37b), $$T_{refl}^{04} \cong \frac{W_{foil}^0 - W_{tape}^0 \left(\frac{\epsilon_{foil}}{\epsilon_{tape}}\right)}{C'_{cam}(1-\epsilon_{foil})}. \tag{37b}$$

The difference between the fourth power of the reflection temperature before and after the flash is now given by equation (38), $$T_{refl}^4 - T_{refl}^{04} \cong \frac{W_{foil} - W_{foil}^0}{C'_{cam}(1-\epsilon_{foil})}. \tag{38}$$

Knowing the camera constant, equation (38) can be evaluated as a function of the post-flash time and then substituted in the image contrast expression of equation (30). The combined steps of using the high reflectivity foil and of using the high emissivity tape is referred to as the "Foil-Tape Method" for the exemplary embodiments described herein.

The surface temperature evolution data can be obtained using a simulation program such as the previously mentioned ThermoCalc software. The IRFT data acquisition using a radiometric camera that accounts for the transient reflection temperature can provide the surface temperature evolution data. Currently, this feature is not available in IR cameras. Here, the exemplary embodiments provide an IR measurement method so that measurement of the transient surface temperature can be performed by the IR radiometric cameras. The change in the pixel intensity at the foil ROI may be defined as expressed in equation (39), $$\Delta W_{foil} = W_{foil} - W_{foil}^0. \tag{39}$$

Using equations (30), (38), and (39), the estimated image contrast expression using the highly reflective foil is given by equation (40), $$\overline{C}_W^t \cong \frac{\varepsilon\left((T^4 - T^{0^4}) - (T_{ref}^4 - T_{ref}^{0^4})\right)}{\varepsilon\left((T^4 - T^{0^4}) + (T_{ref}^4 - T_{ref}^{0^4})\right) + 2\frac{(1-\varepsilon)\Delta W_{foil}}{C'_{cam}(1-\varepsilon_{foil})}}. \quad (40)$$

A simpler expression for the normalized image contrast will now be derived. From equation (13a), the change in the measurement ROI intensity may be derived as expressed in equation (41), $$\Delta W = C_{cam}\sigma\left[\varepsilon(T-T^0)(T+T^0)(T^2+T^{0^2}) + \right. \\ \left. (1-\varepsilon)(T_{refl} - T_{refl}^0)(T_{refl} + T_{refl}^0)(T_{refl}^2 + T_{refl}^{0^2})\right]. \quad (41)$$

Similarly, the change in the intensity for the reference ROI may be expressed as in equation (42), $$\Delta W_{ref} = C_{cam}\sigma\left[\varepsilon(T_{ref} - T_{ref}^0)(T_{ref} + T_{ref}^0)(T_{ref}^2 + T_{ref}^{0^2}) + \right. \\ \left. (1-\varepsilon)(T_{refl} - T_{refl}^0)(T_{refl} + T_{refl}^0)(T_{refl}^2 + T_{refl}^{0^2})\right]. \quad (42)$$

The difference between the change in the measurement ROI intensity and the change in the reference ROI intensity may be expressed as in equation (43), $$\Delta W - \Delta W_{ref} = C_{cam}\sigma\left[\varepsilon(T-T^0)(T+T^0)(T^2+T^{0^2}) - \right. \\ \left. \varepsilon(T_{ref} - T_{ref}^0)(T_{ref} + T_{ref}^0)(T_{ref}^2 + T_{ref}^{0^2})\right]. \quad (43)$$

The sum of the change in the measurement ROI intensity and the change in the reference ROI intensity may be expressed as in equation (44), $$\Delta W + \Delta W_{ref} = C_{cam}\sigma\left[\varepsilon(T-T^0)(T+T^0)(T^2+T^{0^2}) + \right. \\ \varepsilon(T_{ref} - T_{ref}^0)(T_{ref} + T_{ref}^0)(T_{ref}^2 + T_{ref}^{0^2}) + \\ \left. 2(1-\varepsilon)(T_{refl} - T_{refl}^0)(T_{refl} + T_{refl}^0)(T_{refl}^2 + T_{refl}^{0^2})\right]. \quad (44)$$

Assuming that the difference between the reference and measurement temperature is small (e.g., ≤5 K) at the time of maximum contrast, then the expression in equation (45) may be shown, $$(T+T^0)(T^2+T^{0^2}) \cong \\ (T_{ref} + T_{ref}^0)(T_{ref}^2 + T_{ref}^{0^2}) \cong (T_{refl} + T_{refl}^0)(T_{refl}^2 + T_{refl}^{0^2}). \quad (45)$$

Therefore, using equations (43) and (44) the expression in equation (46) may be shown, $$\frac{\Delta W - \Delta W_{ref}}{\Delta W + \Delta W_{ref}} \cong \frac{[\varepsilon(T-T^0) - \varepsilon(T_{ref} - T_{ref}^0)]}{[\varepsilon(T-T^0) + \varepsilon(T_{ref} - T_{ref}^0) + 2(1-\varepsilon)(T_{refl} - T_{refl}^0)]}. \quad (46)$$

Using equation (20), equation (46) may be written as expressed in equation (47), $$\overline{C}_W^t \cong \frac{(\Delta T - \Delta T_{ref})}{[(\Delta T + \Delta T_{ref}) + 2(1-\varepsilon)\Delta T_{refl}]}, \quad (47)$$

where the change in reflection temperature is expressed in equation (48), $$\Delta T_{refl} = (T_{refl} - T_{refl}^0). \quad (48)$$

Therefore, equation (47) may be written as expressed in equation (49), $$\overline{C}_W^t \cong \frac{(\Delta T - \Delta T_{ref})}{\left[(\Delta T + \Delta T_{ref}) + 2\left(\frac{1}{\varepsilon} - 1\right)\Delta T_{refl}\right]}. \quad (49)$$

Using the definition of the temperature contrast of equation (23), the method arrives at the normalized image contrast expression of equation (50), $$\overline{C}_W^t \cong \frac{\overline{C}^t}{\left[1 + \frac{2\left(\frac{1}{\varepsilon} - 1\right)\Delta T_{refl}}{(\Delta T + \Delta T_{ref})}\right]}. \quad (50)$$

Next, equation (50) may be rearranged for the normalized temperature contrast expressed in equation (51), $$\overline{C}^t \cong \left[1 + \frac{2\left(\frac{1}{\varepsilon} - 1\right)\Delta T_{refl}}{(\Delta T + \Delta T_{ref})}\right]\overline{C}_W^t. \quad (51)$$

Thus, the normalized image (pixel intensity) contrast and the normalized temperature contrast can be approximately related to each other. An expression for the normalized pixel intensity contrast to normalized temperature (or pixel intensity/temperature) contrast ratio ε' may be expressed as given in equation (52), $$\varepsilon' \cong \frac{1}{\left[1 + \frac{2\left(\frac{1}{\varepsilon} - 1\right)\Delta T_{refl}}{(\Delta T + \Delta T_{ref})}\right]}, \quad (52)$$

and an expression for the relationship between the normalized image contrast and the normalized temperature contrast may be written as expressed in equation (53), $$\overline{C}_W^t \cong \varepsilon'\overline{C}^t. \quad (53)$$

The pixel/temperature contrast ratio indicates that the reflection temperature rise (caused by flash decay), the object temperature rise (due to the flash power during rise time), and the emissivity affect the conversion between the two contrasts. The reflection temperature is due to the glass shield and the flash lamps. An estimated amount of less than 50% of the flash energy comes through the glass shield of the flash lamps during the flash duration. The remaining energy comes through the glass shield as the flash lamps continue to glow after the flash, providing an increase in the reflection temperature. Similarly, the, glass casing of the bulb and the glass shield get hot during the flash and continue to provide thermal radiation. Some flash-hood designs use fans to cool the lamps after the flash to reduce the amount of heat from afterglow. Assuming that the reflection temperature is the same as the ambient temperature immediately after the flash, then equation (53) may be simplified to the expression in equation (54), $$\overline{C}^t \cong \overline{C}_W^t. \tag{54}$$

A shutter that covers the flash lamps immediately after the flash can be used to achieve a constant reflection temperature. In practice, $\Delta T_{refl}$ is positive and the image contrast and the temperature contrast would differ unless the object has an emissivity value of one. Now, equations to compute temperatures at the measurement ROI and the reference ROI using the measured ROI intensities will be derived. From equations (27) and (31), the temperature at the measurement ROI is given by equation (55a), $$T = \left( \frac{\frac{W}{W_{tape}^0} \varepsilon_{tape} T_{tape}^{0^4} - (1-\varepsilon) T_{refl}^4}{\varepsilon} \right)^{0.25} \tag{55a}$$

In equation (55a), all quantities are known or measured except the reflection temperature. The reflection temperature is derived from equation (35) and may be expressed as in equation (55b):

$$T_{refl}^4 \cong \frac{W_{foil} - W_{tape}^0 \left( \frac{\varepsilon_{foil}}{\varepsilon_{tape}} \right)}{\frac{W_{tape}^0}{T_{tape}^{0^4}} \left( \frac{1-\varepsilon_{foil}}{\varepsilon_{tape}} \right)}. \tag{55b}$$

The pre-flash temperature at the measurement ROI is given by equation (56), $$T^0 = \left( \frac{\varepsilon_{tape} \frac{W^0}{W_{tape}^0} T_{tape}^{0^4} - (1-\varepsilon) T_{refl}^{0^4}}{\varepsilon} \right)^{0.25}. \tag{56}$$

In equation (56), all quantities are known or measured except the pre-flash reflection temperature, which is given by equation (37b). Similarly, the temperature at the reference ROI is given by equation (57), $$T_{ref} = \left( \frac{\varepsilon_{tape} \frac{W_{ref}}{W_{tape}^0} T_{tape}^{0^4} - (1-\varepsilon) T_{refl}^4}{\varepsilon} \right)^{0.25}. \tag{57}$$

Similarly, the pre-flash temperature at the reference ROI is given by equation (58), $$T_{ref}^0 = \left( \frac{\varepsilon_{tape} \frac{W_{ref}^0}{W_{tape}^0} T_{tape}^{0^4} - (1-\varepsilon) T_{refl}^{0^4}}{\varepsilon} \right)^{0.25}. \tag{58}$$

Using equation (55a) through equation (58) and equation (23) through equation (25), the temperature contrast may be computed. Thus, the temperature contrast may be calculated using the ROSE intensity provided by the IR camera. The formula assumes that the half-max width at the measurement and reference point is at least four times the width of the respective ROIs so that the ROI intensity provided by the camera is close to the maximum intensity possible for the given temperature.

The accuracy of the estimation of the temperature contrast from the measured pixel intensity data is quite sensitive to the value of the surface emissivity of the test object. In one embodiment, the method assumes that the emissivity of the measurement ROI and the reference ROI are the same. In another embodiment, the method can either independently measure emissivity or use a recommended value. Another approach to determine emissivity from the IRFT data taken with the foil and the tape on the test object starts with the relationship between the pixel intensity and the temperature for the foil and the tape. Using equation (36), the method in one embodiment can represent the pre-flash pixel intensity of the foil and the tape as in equation (59) and equation (60), respectively, $$W_{foil}^0 = C_{cam} \sigma((1-\epsilon_{foil}) T_{refl}^{0^4} + \epsilon_{foil} T_{tape}^{0^4}) \text{ and} \tag{59}$$

$$W_{tape}^0 \cong C_{cam} \sigma(\epsilon_{tape} T_{tape}^{0^4} + (1-\epsilon_{tape}) T_{refl}^{0^4}). \tag{60}$$

Equations (59) and (60) may then be arranged as expressed in equations (61) and (62), $$\frac{W_{tape}^0}{(1-\varepsilon_{tape})} \cong C_{cam} \sigma \left( \frac{\varepsilon_{tape} T_{tape}^4}{(1-\varepsilon_{tape})} + T_{refl}^{0^4} \right) \text{ and} \tag{61}$$

$$\frac{W_{foil}^0}{(1-\varepsilon_{foil})} = C_{cam} \sigma \left( T_{refl}^{0^4} + \frac{\varepsilon_{foil} T_{tape}^4}{(1-\varepsilon_{foil})} \right). \tag{62}$$

Equations (61) and (62) may then be combined to express equations (63), (64), and (65), $$\frac{W_{tape}^0}{(1-\varepsilon_{tape})} - \frac{W_{foil}^0}{(1-\varepsilon_{foil})} = C_{cam} \sigma \left( \frac{\varepsilon_{tape} T_{tape}^4}{(1-\varepsilon_{tape})} - \frac{\varepsilon_{foil} T_{tape}^4}{(1-\varepsilon_{foil})} \right), \tag{63}$$

$$\frac{W_{tape}^0}{(1-\varepsilon_{tape})} - \frac{W_{foil}^0}{(1-\varepsilon_{foil})} = C_{cam} \sigma \left( \frac{\varepsilon_{tape}}{(1-\varepsilon_{tape})} - \frac{\varepsilon_{foil}}{(1-\varepsilon_{foil})} \right) T_{tape}^4, \text{ and} \tag{64}$$

$$C'_{cam} T_{tape}^{0^4} = C_{cam} \sigma T_{tape}^{0^4} = \frac{\left( \frac{W_{tape}^0}{(1-\varepsilon_{tape})} - \frac{W_{foil}^0}{(1-\varepsilon_{foil})} \right)}{\left( \frac{\varepsilon_{tape}}{(1-\varepsilon_{tape})} - \frac{\varepsilon_{foil}}{(1-\varepsilon_{foil})} \right)}. \tag{65}$$

Equation (65) provides a more precise expression for the camera constant defined in equation (33). Equations (59) and (60) may then be arranged as expressed in equations (66) and (67), $$\frac{W_{tape}^0}{\varepsilon_{tape}} \cong C'_{cam}\left(T_{tape}^{0^4} + \frac{(1-\varepsilon_{tape})T_{refl}^{0^4}}{\varepsilon_{tape}}\right) \text{ and} \qquad (66)$$

$$\frac{W_{foil}^0}{\varepsilon_{foil}} = C'_{cam}\left(\frac{(1-\varepsilon_{foil})T_{refl}^{0^4}}{\varepsilon_{foil}} + T_{tape}^{0^4}\right). \qquad (67)$$

Equations (66) and (67) may then be combined and expressed as in equation (68), $$\frac{W_{tape}^0}{\varepsilon_{tape}} - \frac{W_{foil}^0}{\varepsilon_{foil}} \cong C_{cam}\sigma\left(\frac{(1-\varepsilon_{tape})T_{refl}^{0^4}}{\varepsilon_{tape}} - \frac{(1-\varepsilon_{foil})T_{refl}^{0^4}}{\varepsilon_{foil}}\right). \qquad (68)$$

Equations (64) and (68) may then be combined and expressed as in equations (69) and (70), $$\frac{\left(\frac{W_{tape}^0}{\varepsilon_{tape}} - \frac{W_{foil}^0}{\varepsilon_{foil}}\right)}{\left(\frac{W_{tape}^0}{(1-\varepsilon_{tape})} - \frac{W_{foil}^0}{(1-\varepsilon_{foil})}\right)} \cong \frac{\left(\frac{(1-\varepsilon_{tape})}{\varepsilon_{tape}} - \frac{(1-\varepsilon_{foil})}{\varepsilon_{foil}}\right)T_{refl}^{0^4}}{\left(\frac{\varepsilon_{tape}}{(1-\varepsilon_{tape})} - \frac{\varepsilon_{foil}}{(1-\varepsilon_{foil})}\right)T_{tape}^{0^4}} \text{ and} \qquad (69)$$

$$\frac{\left(\frac{W_{tape}^0}{\varepsilon_{tape}} - \frac{W_{foil}^0}{\varepsilon_{foil}}\right)}{\left(\frac{W_{tape}^0}{(1-\varepsilon_{tape})} - \frac{W_{foil}^0}{(1-\varepsilon_{foil})}\right)} \cong -\frac{(1-\varepsilon_{tape})}{\varepsilon_{tape}} \frac{(1-\varepsilon_{foil})}{\varepsilon_{foil}} \frac{T_{refl}^{0^4}}{T_{tape}^{0^4}}. \qquad (70)$$

Next, equation (70) may be rearranged and a quantity J may expressed as in equation (71), $$J = \frac{T_{refl}^{0^4}}{T_{tape}^{0^4}} = \frac{\left(\frac{W_{tape}^0}{\varepsilon_{tape}} - \frac{W_{foil}^0}{\varepsilon_{foil}}\right)}{\left(\frac{W_{tape}^0}{(1-\varepsilon_{tape})} - \frac{W_{foil}^0}{(1-\varepsilon_{foil})}\right)\left(-\frac{(1-\varepsilon_{tape})}{\varepsilon_{tape}}\frac{(1-\varepsilon_{foil})}{\varepsilon_{foil}}\right)}. \qquad (71)$$

Further, a quantity B may be denoted as expressed in equation (72), $$B = \frac{\left(\frac{W_{tape}^0}{(1-\varepsilon_{tape})} - \frac{W_{foil}^0}{(1-\varepsilon_{foil})}\right)}{\left(\frac{\varepsilon_{tape}}{(1-\varepsilon_{tape})} - \frac{\varepsilon_{foil}}{(1-\varepsilon_{foil})}\right)}. \qquad (72)$$

Equations (65) and (72) may then be combined and expressed as in equation (73), $$B = C'_{cam}T_{tape}^{0^4}. \qquad (73)$$

The camera constant is given by the representation in equation (74), $$C'_{cam} = \frac{\left(\frac{W_{tape}^0}{(1-\varepsilon_{tape})} - \frac{W_{foil}^0}{(1-\varepsilon_{foil})}\right)}{\left(\frac{\varepsilon_{tape}}{(1-\varepsilon_{tape})} - \frac{\varepsilon_{foil}}{(1-\varepsilon_{foil})}\right)} \frac{1}{T_{tape}^{0^4}}. \qquad (74)$$

The pre-flash temperature at the measurement ROI is given by equation (75), $$W^0 \cong C_{cam}\sigma(\varepsilon T^{0^4} + (1-\varepsilon)T_{refl}^{0^4}). \qquad (75)$$

Due to some noted observations and assumptions, including contact of the tape with the test object, the steady state of surface temperature before flash, and the reflection temperature not differing more than 5 K from the test object temperature before flash, it may be presumed that equation (76) holds $$T^0 \cong T_{tape}^0. \qquad (76)$$

Equation (76) may then be substituted into equation (75), resulting in the expressions of equations (77), (78), (79), and (80), $$W^0 \cong C_{cam}\sigma(\varepsilon T_{tape}^{0^4} + (1-\varepsilon)T_{refl}^{0^4}). \qquad (77)$$

$$W^0 \cong C_{cam}\sigma T_{tape}^{0^4}\left(\varepsilon + (1-\varepsilon)\frac{T_{refl}^{0^4}}{T_{tape}^{0^4}}\right), \qquad (78)$$

$$W^0 \cong B(\varepsilon + 1 - \varepsilon)J, \text{ and} \qquad (79)$$

$$\varepsilon \cong \frac{\frac{W^0}{B} - J}{1 - J}. \qquad (80)$$

Thus, the emissivity of the test object at the room temperature can be estimated by an embodiment described herein. If the measurement is done at two different ambient temperatures that are at least 5 K apart, the method may provide better confidence in the average emissivity measurement.

Figure 3:
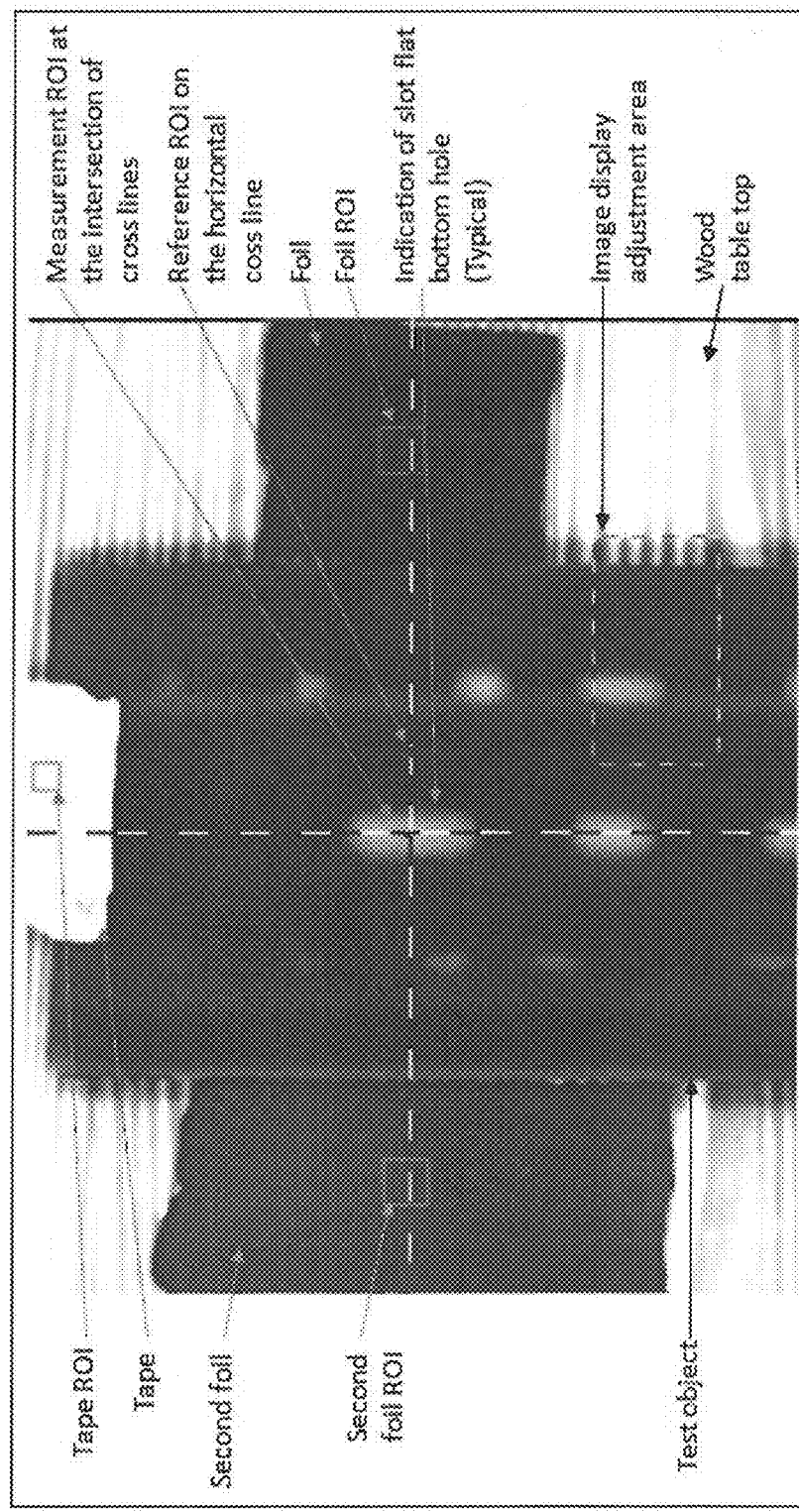
FIG. 3 is an infrared image of a plate with back drilled flat bottom slots along with foils and tape (post-flash time=0.6 sec), in accordance with some embodiments described herein.

This example illustrates the steps for converting the normalized image contrast from the thermography data to the normalized temperature contrast using additional measurements required for determining the reflection temperature. In one embodiment, the test object may comprise back-drilled elongated flat bottom slots or holes at various depths. FIG. 3 shows the IRFT image of a test object that is made of reinforced carbon-carbon (RCC) with back drilled flat bottom slots and with foil and tape (post-flash time=0.6 sec). The method in this example is interested in a measurement on the center slot. The locations of the measurement and reference ROIs are indicated in FIG. 3. One piece of the wrinkled aluminum foil is placed on the left side of the test object and the other piece of an identical foil is placed on the right side of the test object. The locations of the foil ROT are indicated. A high emissivity adhesive tape is affixed at the top of the test object The tape ROI is indicated in FIG. 3, The image frame time is extremely close to the peak contrast time. The image indicates normalized pixel intensity. The image display of the contrast is adjusted by manipulating the display rectangle location and size. In this example, the measurement ROI is a single pixel (or simply 1×1 pixel). The sizes of the ROIs are provided in the Table I. A 1×1 pixel in dimensions is equal to 0.023 in.×0.023 in. Normally, ROI cursors and lines have colors for quick identification, but colors are not necessary in this description.

TABLE I

Pixel Size of Region of Interests

| Region of Interest | Pixel Size |
|---|---|
| Measurement | 1 × 1 |
| Reference | 3 × 3 |
| Foil 2 | 15 × 15 |
| Foil 1 | 15 × 15 |
| Tape | 9 × 9 |

Figure 4:
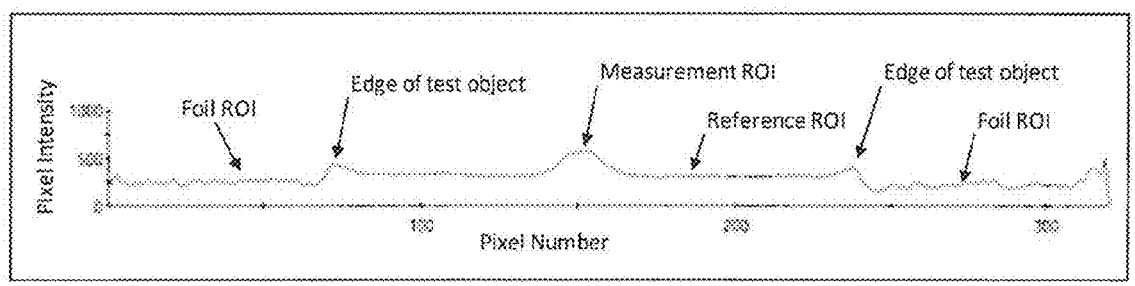
FIG. 4 is a graph of the value of pixel intensity as a function of position along a horizontal cross line in a frame taken at 0.6 seconds after the flash, in accordance with some embodiments described herein.

The dashed cross lines of FIG. 3 are used to plot the pixel intensity along the lines to locate the peak point and the baseline intensity for the selection of the measurement and reference ROIs. FIG. 4 shows a plot of pixel intensity along the horizontal pixel line taken in a frame at post-flash time of 0.6 seconds. Various ROIs, such as the foil, measurement, and reference ROI, are also identified in FIG. 4.

Table II gives the pre-flash measurements and emissivity inputs. Note that the representation of Eq. (80) is applied to the Table II data (except for the test object emissivity). The test object emissivity in this example is estimated to be 0.75 at the measurement ROI. A significant number of such measurements would improve confidence in the value. Therefore, the method may instead use an emissivity value of 0.78, which is the value published in the literature for the object material.

TABLE II

Pre-flash Measurements and Emissivity Inputs

| | |
|---|---|
| $T_{ref}^0$ (K) | 300 |
| $T_{tape}^0$ (K) | 296 |
| $\epsilon_{tape}$ | 0.99 |
| $\epsilon_{foil}$ | 0.05 |
| $\epsilon$ | 0.78 |
| $W_{tape}^0$ (average bit value) | 6382 |
| $W_{foil}^0$ (average bit value) | 6768 |
| $W_{ref}^0$ (average bit value) | 6480 |

Figure 5:
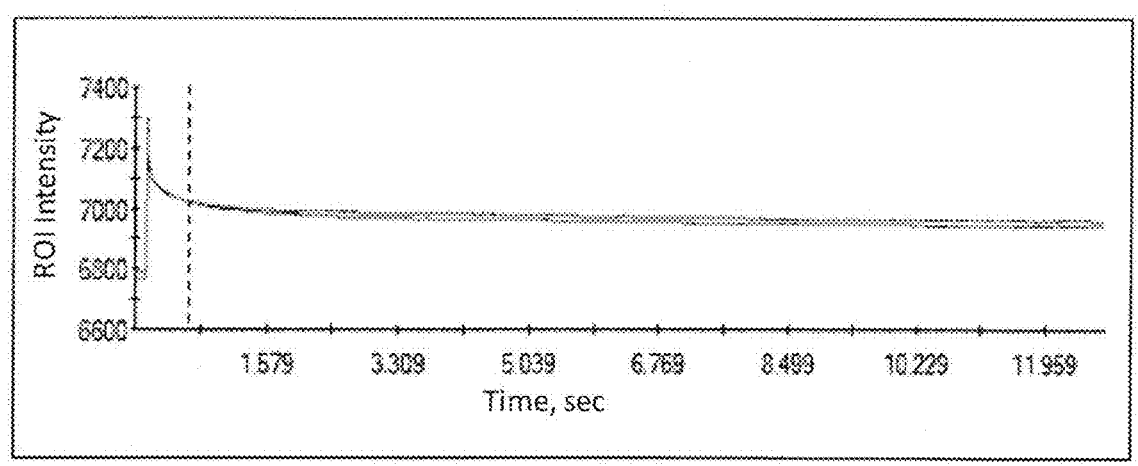
FIG. 5 is a graph of the pixel intensity evolution as a function of time on the foil ROI (lower evolution from the left foil ROI and upper evolution from the right foil ROI) with the peak time of 0.6 seconds indicated by the dashed vertical line, in accordance with some embodiments described herein.

FIG. 5 provides plots of the pixel intensity evolutions of the two foil ROIs. The vertical dotted line at time equal to 0.6 seconds indicates the peak contrast time. The foils are reflective but specular reflectivity is undesirable. Moreover, the test object is also diffusely reflective. The two foils provide two independent measurements of the pixel intensity evolution. The two intensity evolutions agree with each other and an average value is chosen. The two foils are on either side of the measurement/reference ROI. Thus, an average of the two foil intensity evolutions provides an estimate of foil intensity evolution in the measurement/reference ROI with better confidence as opposed to choosing a single foil intensity evolution.

Figure 6:
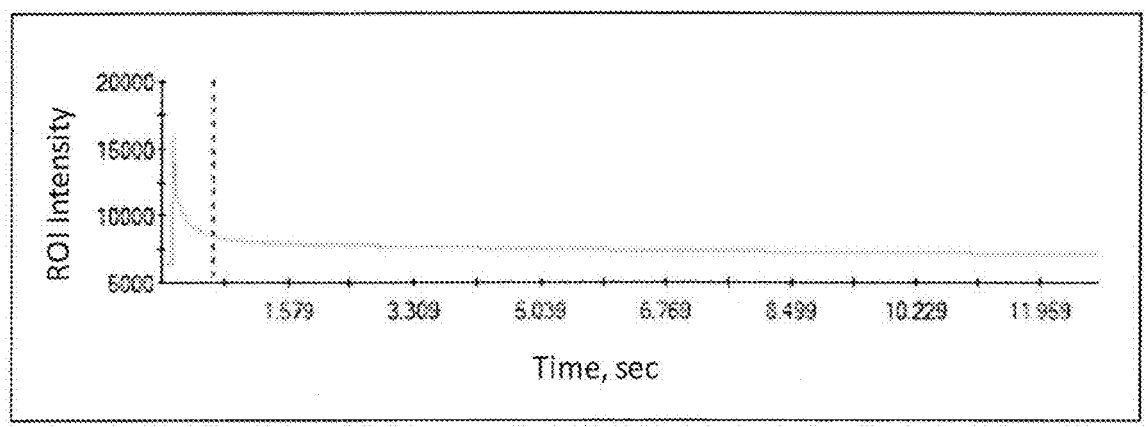
FIG. 6 is a graph of the pixel intensity evolution as a function of time for the tape ROI, in accordance with some embodiments described herein.

FIG. 6 shows the pixel intensity evolution at the tape ROI. The flash duration is set to 0.003 seconds. The time between the image frames is 0.017 seconds for a frame rate of 60 frames/second. The intensity decays quite rapidly before the capture of the first post-flash frame. The test object reaches the maximum temperature at the end of the flash duration, but the camera is incapable of capturing the corresponding peak intensity due to the slow frame rate. FIG. 6 indicates that the temperature rise is higher on the tape ROI than that on the foil ROI. The tape ROI is in the area of tape overhang and indicates similar intensity evolution as that of the foil ROI.

Figure 7:
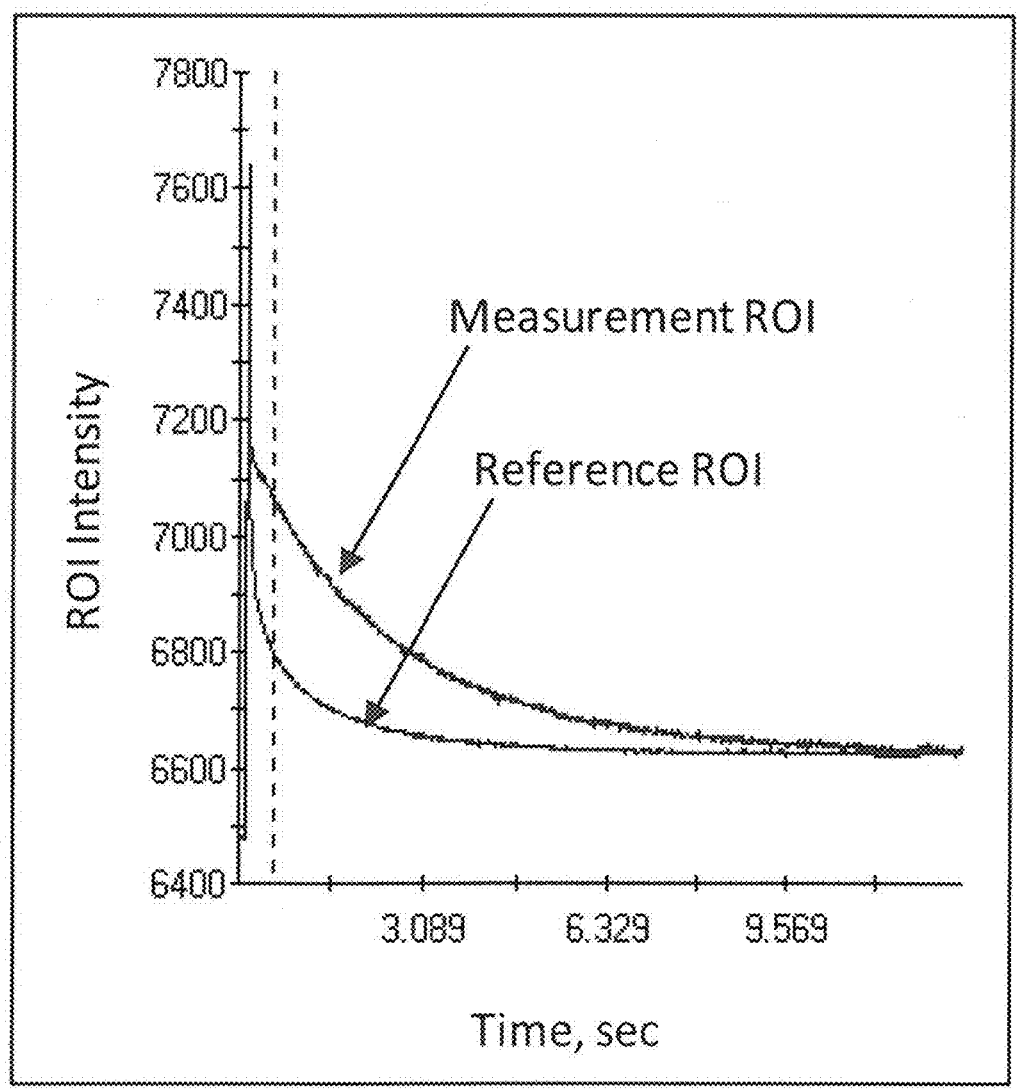
FIG. 7 is a graph of the ROI intensity evolutions for the measurement (upper evolution) ROI and the reference (lower evolution) ROI, in accordance with some embodiments described herein.

FIG. 7 shows the pixel intensity evolution at the measurement (upper curve) and the reference (lower curve) ROI. FIG. 7 indicates the hot spot (higher intensity) of the measurement ROI in comparison to the reference ROI. The two traces for the measurement ROI and the reference ROI eventually merge together as the temperature of the indication area and the surrounding area become equal.

Figure 8:
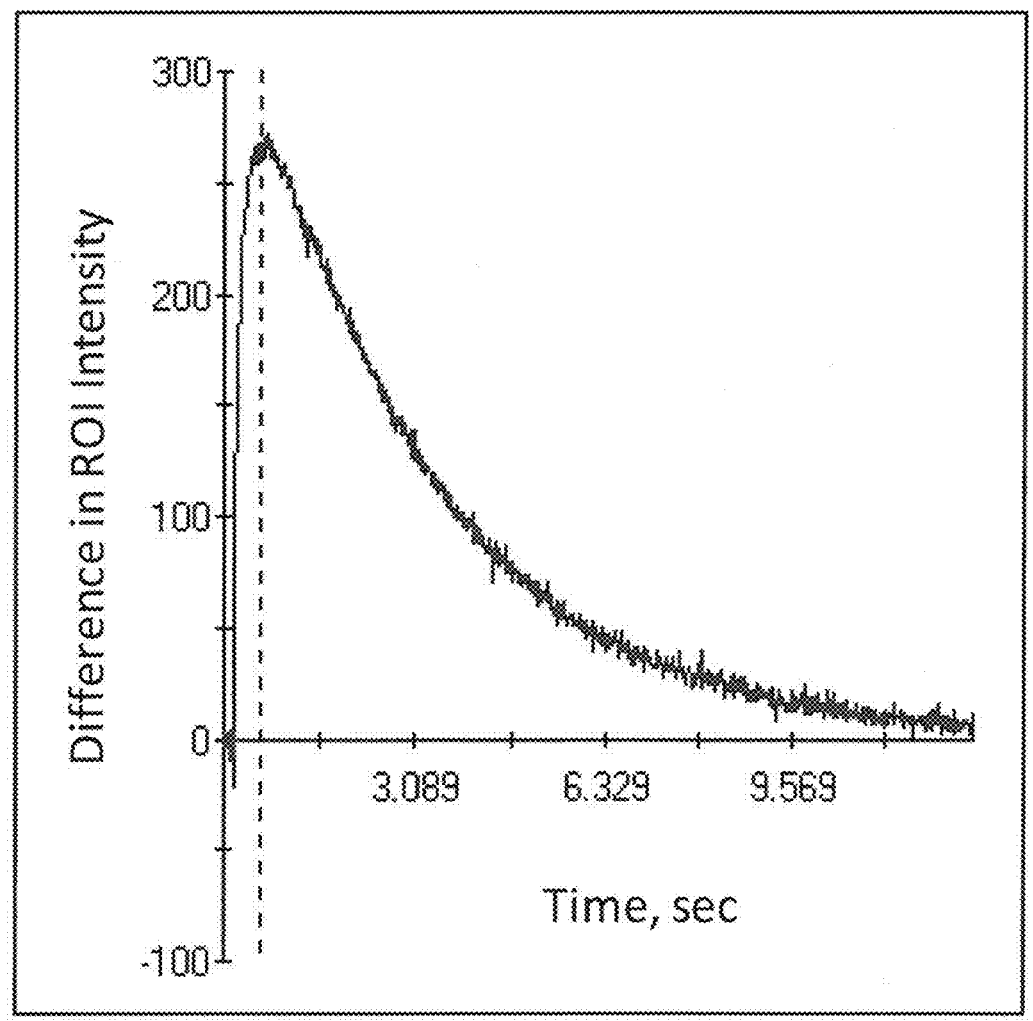
FIG. 8 is a graph of simple contrast evolution at the measurement ROI with the peak time of 0.5 seconds indicated by the dashed vertical line, in accordance with some embodiments described herein.

FIG. 8 shows a plot of a simple image contrast, which is defined as the difference between the intensities of measurement and reference ROIs. The simple contrast evolution at the measurement ROI, indicates a peak time of approximately 0.5 seconds.

Figure 9:
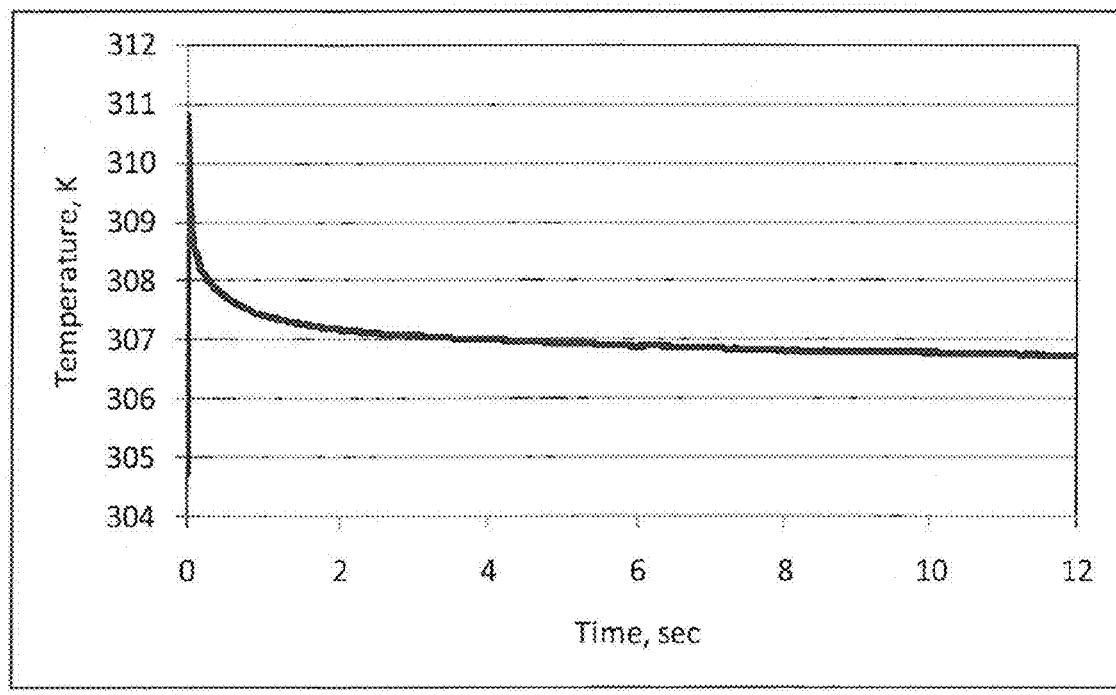
FIG. 9 is a graph of computed evolution of the reflection temperature, in accordance with some embodiments described herein.
Figure 10:
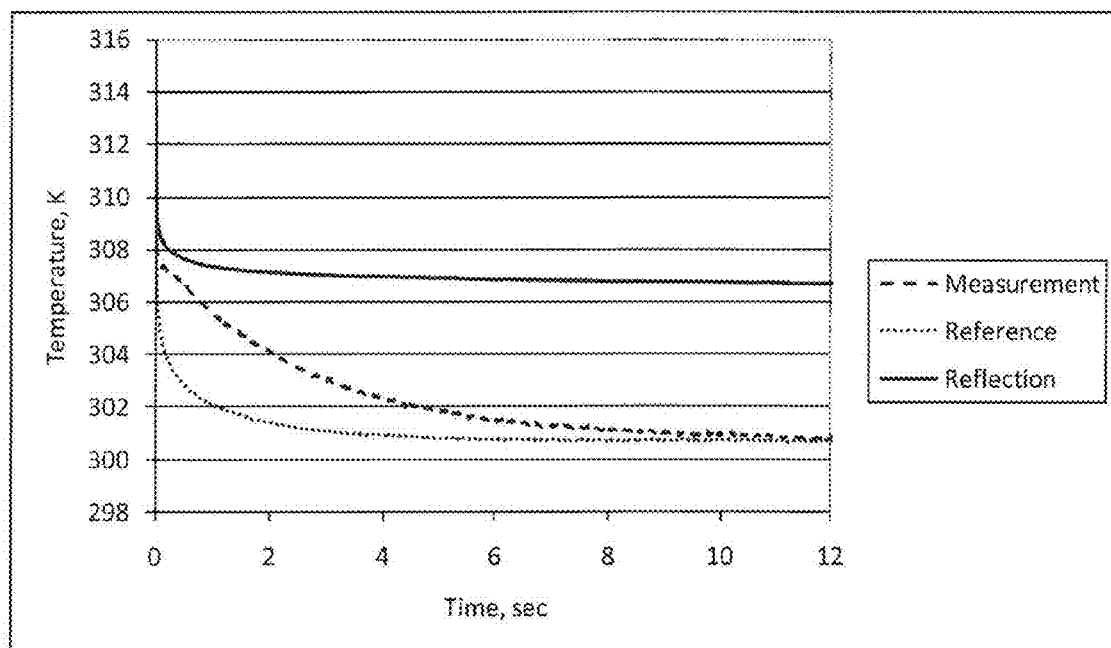
FIG. 10 is a graph of estimated temperature evolutions for the measurement ROI (middle curve), the reference ROI (bottom curve), and the reflection or the background ROI (top curve), in accordance with some embodiments described herein.
Figure 11A:
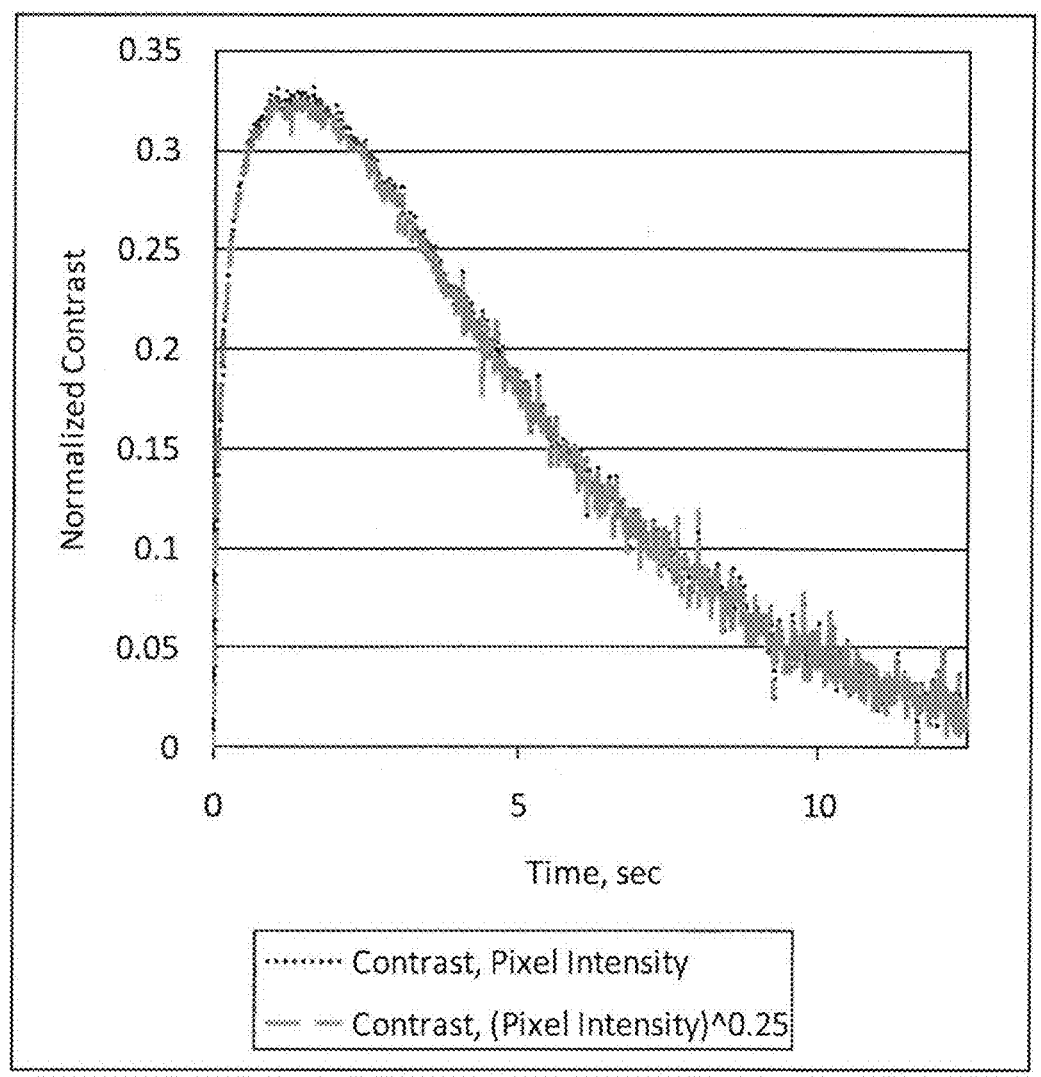
FIG. 11(a) is a graph of normalized image contrast computed using the pixel intensity (upper curve) and one fourth power of the pixel intensity, in accordance with some embodiments described herein.
Figure 11B:
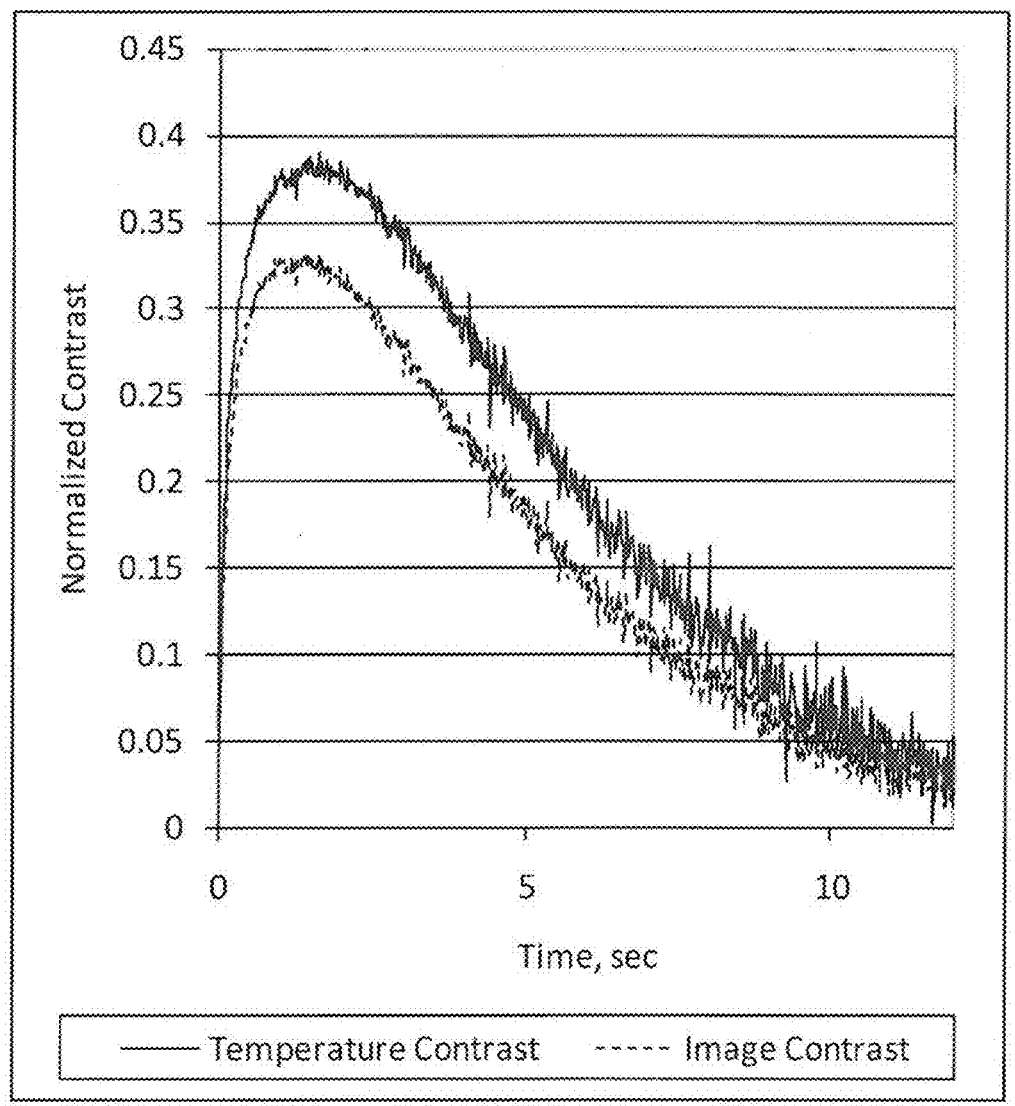
FIG. 11(b) is a graph of measured normalized image contrast (lower curve) and estimated normalized temperature contrast (upper curve), in accordance with embodiments described herein.
Figure 12:
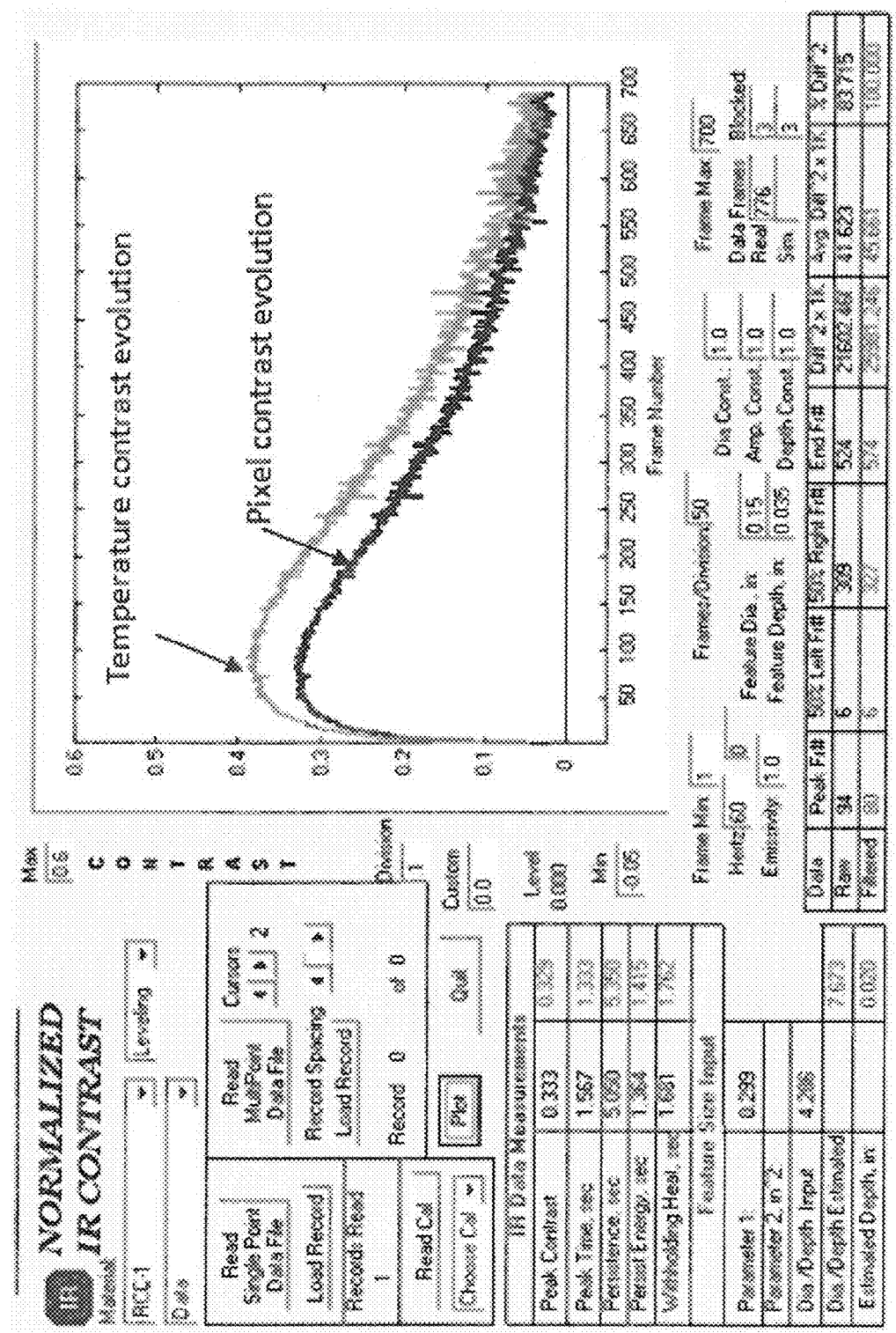
FIG. 12 is an exemplary screen shot displaying normalized temperature contrast evolution (upper curve) and normalized image contrast evolution (lower curve) computed using software that implements simulation and data analysis methods described herein in accordance with some embodiments.
Figure 13:
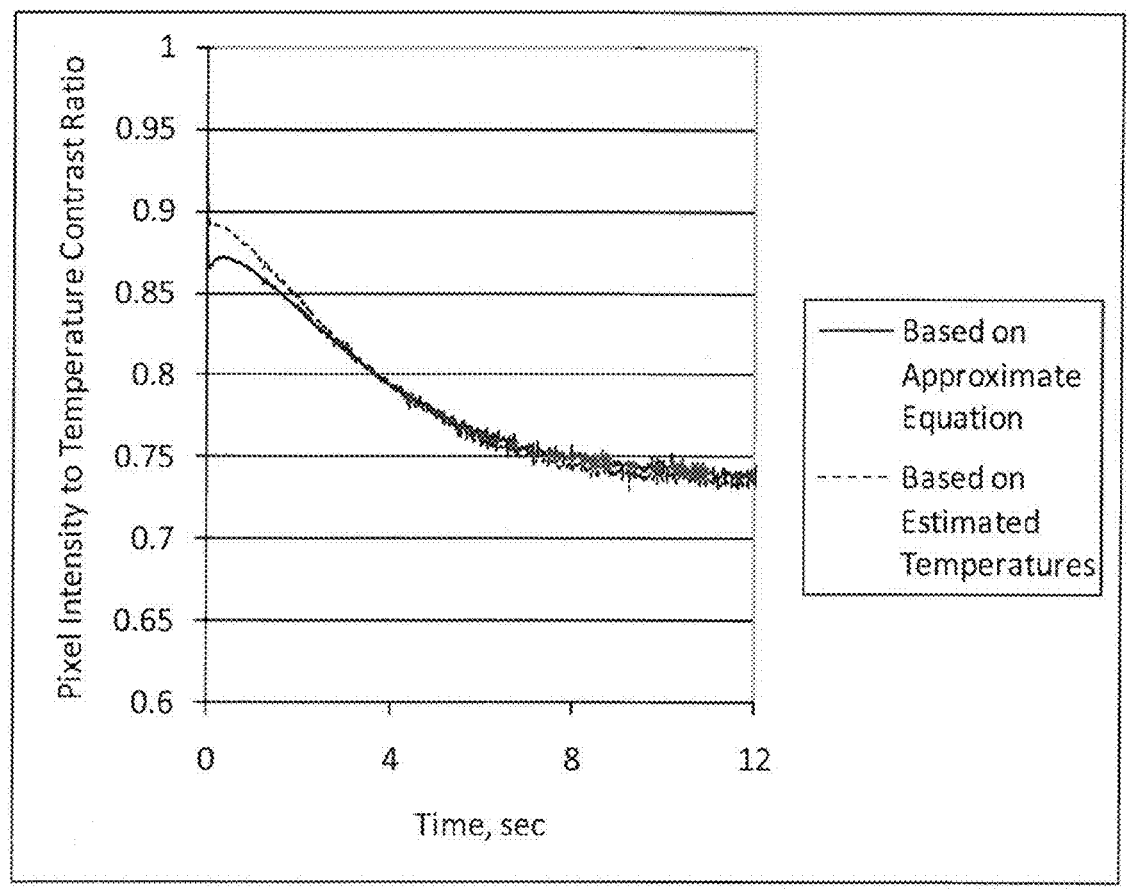
FIG. 13 is a graph of the pixel intensity to temperature contrast ratio, in accordance with some embodiments described herein.

Referring now to FIG. 9, this embodiment begins with equation (65) being used to compute the camera constant. Next, equations (37a) and (37b) are used to compute the reflection temperature evolution. FIG. 9 provides an example of a computed reflection temperature evolution. The pre-flash reflection temperature is estimated to be about 305 K, which is 5 K above the pre-flash temperature of the test object. Also, the reflection temperature is 2 K higher than the pre-flash reflection temperature. When the data for this example was taken, the setup was used to acquire five other shots within 5 minutes before this represented shot, and the time between the last shot and the current one was less than a minute. Thus, the flash lamps were warmer than the ambient temperature before the flash and caused the reflection temperature to be higher than the ambient temperature. In at least one of the embodiments described herein, the method computes the measurement temperature evolution using equation (55a). Using equation (57), the method also computes the reference temperature evolution. The three estimated temperature evolutions are shown together in FIG. 10. The upper curve is for the reflection temperature. The middle curve is for the measurement ROI temperature and the lower curve is for the reference ROI temperature. FIG. 11(a) shows the image contrast computed using the pixel intensity and one fourth ($\frac{1}{4}^{th}$) power of pixel intensity to illustrate equation (45), which suggests that the contrast computed with the fourth power of the temperature and the contrast computed with unity power of the temperature are approximately the same. FIG. 11(b) demonstrates the estimated temperature contrast (upper curve) along with the image contrast (lower curve) with $\epsilon=0.78$. Thus, the pixel and temperature contrast differ, if the test object's emissivity is less than one. FIG. 11(b) also illustrates the difference in the peak contrasts due to lower values of the emissivity. FIG. 12 shows an exemplary screen shot of the steps of computing the temperature contrast evolution (upper curve) and pixel (image) contrast evolution (lower curve) with software implementing the IR Contrast method which relates the thermal measurements in terms of the normalized anomaly contrast as a function of the frame number. FIG. 13 represents the plot of the contrast ratio $\epsilon'$. Two plots are shown. One plot (lower curve) uses the representation given by equation (52). The other plot is the ratio of the two contrasts shown in FIG. 12. The plots differ slightly at early instances of time, but the two values agree well at later times. The contrast ratio is approximately the same as the emissivity of the test object for longer times when the rate of change in the surface temperature is relatively low.

In at least one embodiment, the method estimates the normalized image contrast based on results from the surface temperature simulation of the software sold commercially as ThermoCalc in order to understand the effect of the reflection temperature on the profile of the pixel contrast. In this particular example, the method takes a sample simulation temperature evolution at the measurement and reference areas. The simulation power input is 1.8E6 W/m^2 with a duration setting at 0.003 second. This set-up assumes about 30% efficiency for converting the electrical power (12 kJ source) to the absorbed energy. Depending upon the flash power setting, the reflection temperature evolution is affected. The method of this example estimates the reflection temperature evolution based on the experimental method explained in this description.

Figure 14:
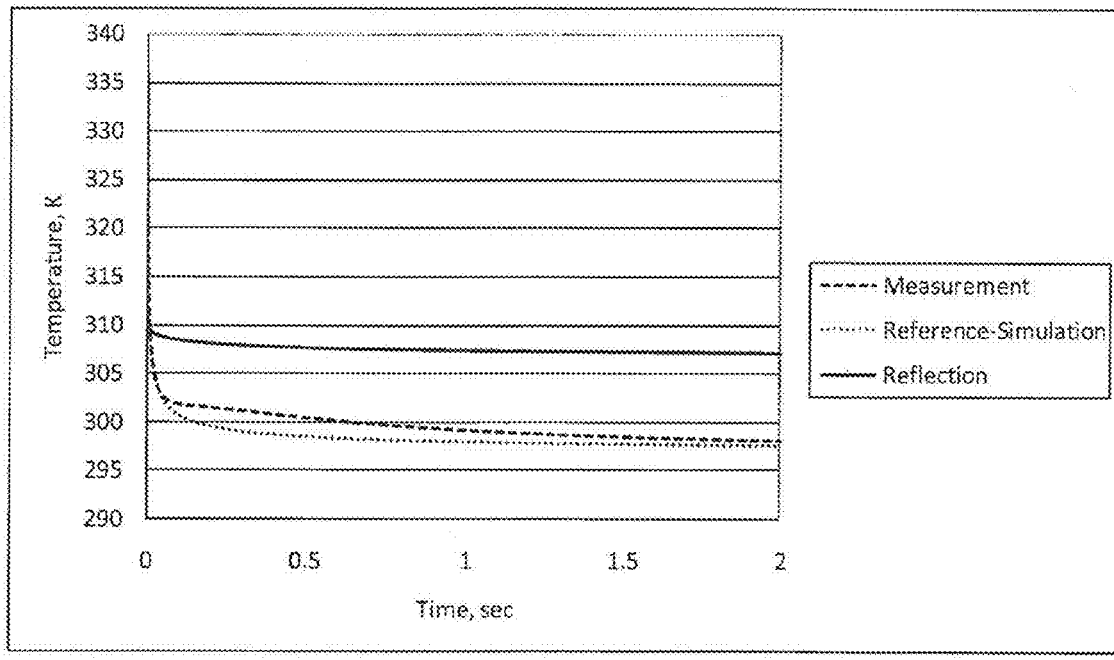
FIG. 14 is a graph of simulated temperature evolutions with an assumed refection temperature evolution, in accordance with some embodiments described herein.
Figure 15:
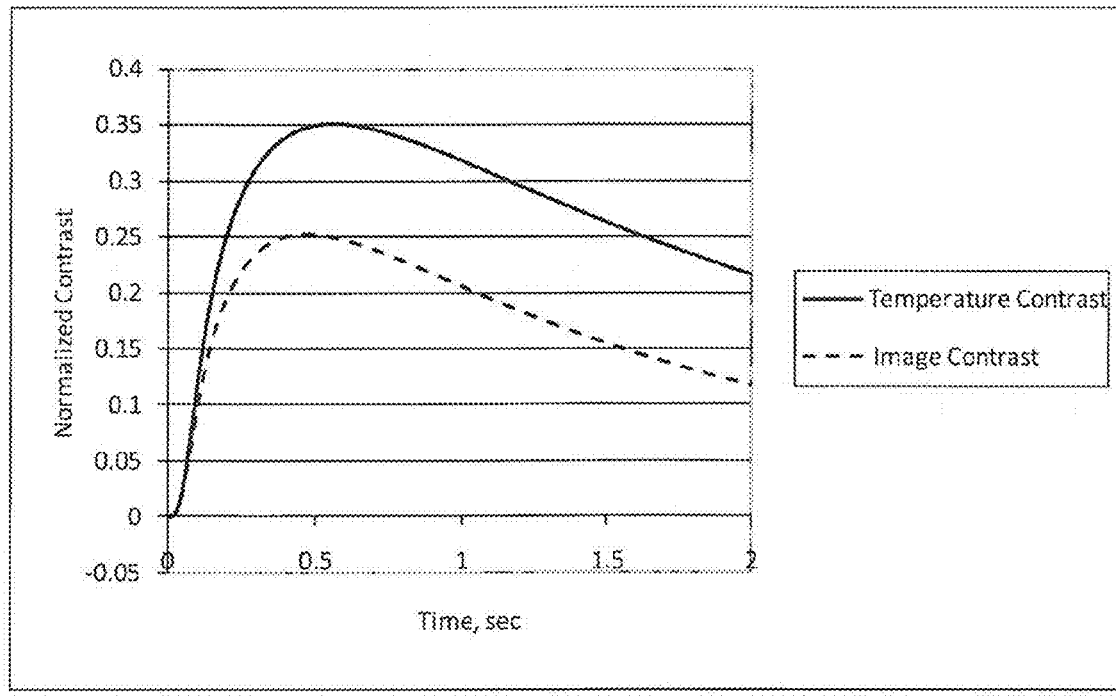
FIG. 15 is a graph of estimated image contrast and of simulated temperature contrast, in accordance with some embodiments described herein.

FIG. 14 shows the simulated temperature evolutions with an assumed reflection temperature evolution. The upper curve represents the reflection temperature. The middle curve is indicative of the measurement ROI temperature and the lower curve is for the reference ROI temperature. The normalized temperature contrast is calculated using the representation given by equation (51). The method of this particular example assumes that the emissivity of the test object equals 0.78. Using equation (30), the method of this example can compute the image contrast. The results are shown in FIG. 15. The upper curve shows the temperature contrast. The lower curve shows the image contrast. Using equation (27), the pixel intensity can be determined if the camera constant is known. Thus, this example illustrates the influence of the emissivity change on the pixel contrast. It also suggests that changes in the pulse power have a small influence on the pixel contrast due to changes in the reflection temperature.

If the method of this particular embodiment assumes that one can input the ambient reflection temperature in the simulation model, then the afterglow of the heat source would be due to differences in the radiation between the pre-flash and post-flash reflection temperature. The afterglow flux may be represented by equation (81), $$S_{postflash} = \sigma(T_{refl}^4 - T_{refl0}^4). \tag{81}$$

Figure 16:
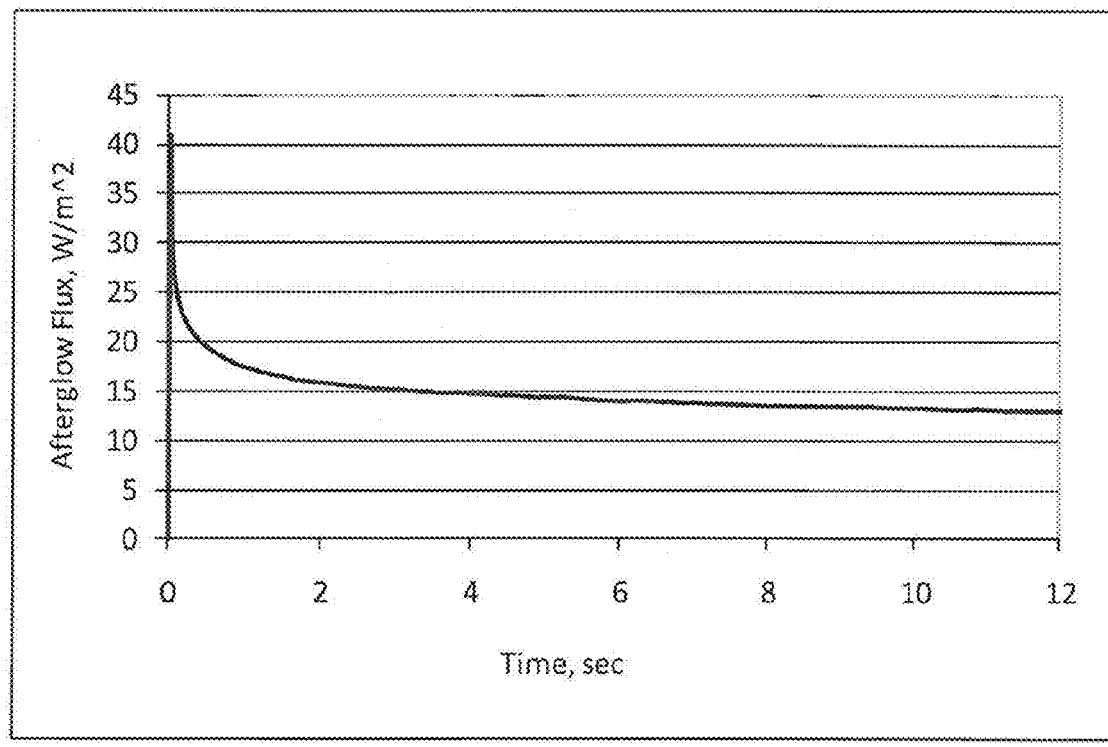
FIG. 16 is a graph of estimated afterglow flux as a function of time charted from the first post-flash frame, in accordance with some embodiments described herein.
Figure 17:
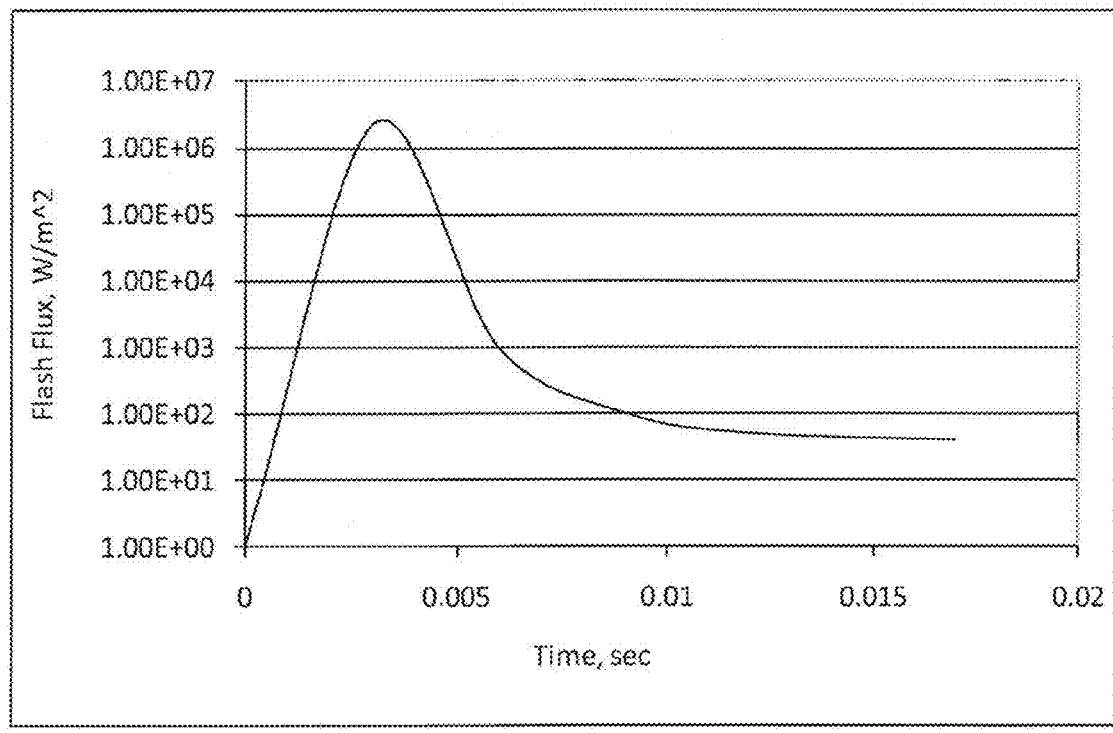
FIG. 17 is a graph of flash flux evolution as a function of time until the first post-flash frame, in accordance with some embodiments described herein.

The afterglow flux evolution starts from the first post-flash frame. The flash lamp pulse flux evolution is estimated for a duration between the start of the flash and the first post-flash frame. An example of afterglow flux evolution is given in FIG. 16. FIG. 17 shows an example of flash flux evolution until the first post-flash frame. The flash lamp pulse and the post-flash afterglow evolutions can be added to model the compound source flux evolution for the entire time of data acquisition.

Figure 18:
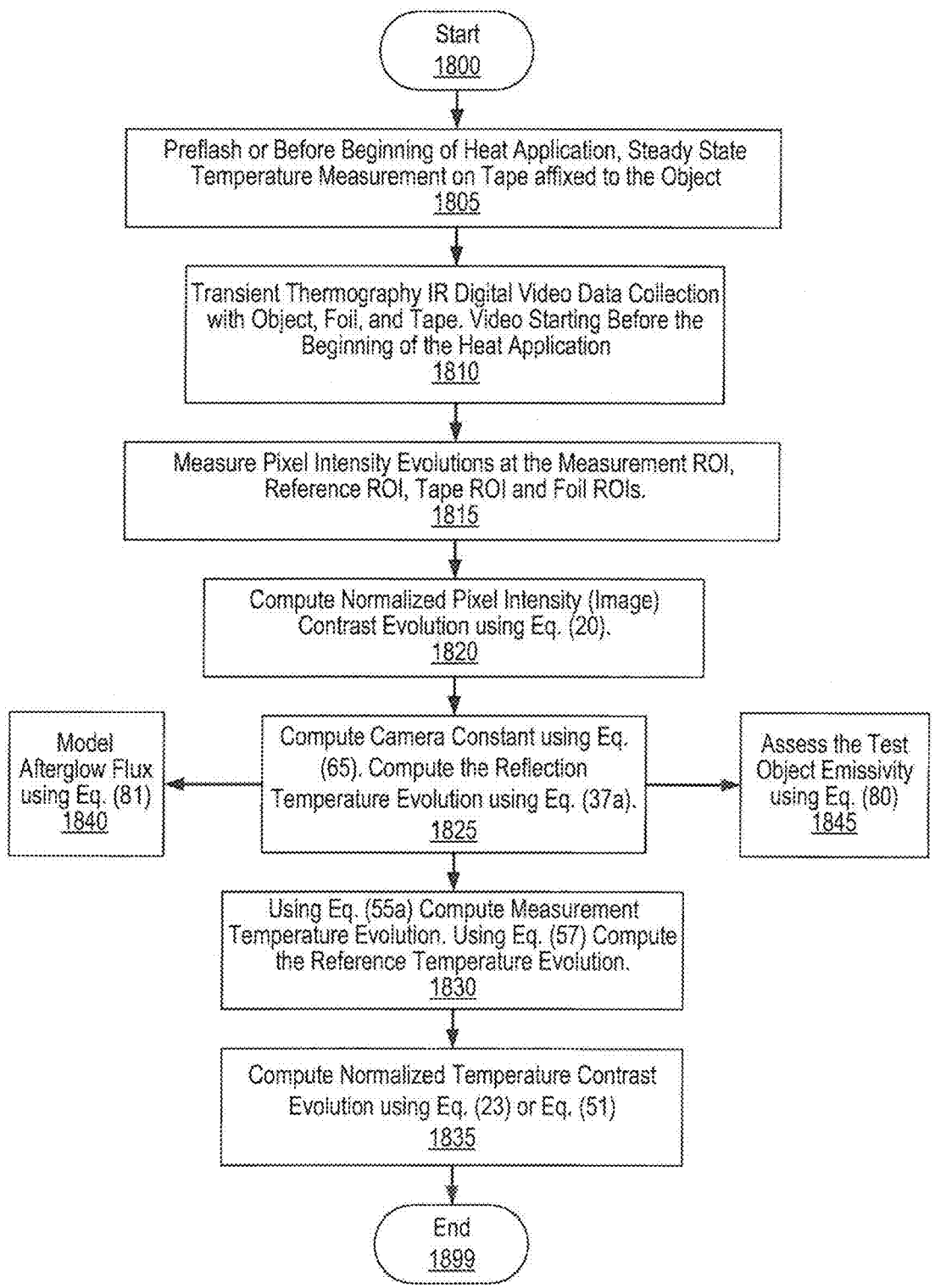
FIG. 18 is a flow diagram illustrating methods for converting an image contrast evolution of an object to a temperature contrast evolution, for modeling afterglow flux, and for assessing the test object emissivity, in accordance with some embodiments described herein.

FIG. 18 is a flow diagram illustrating methods for converting an image contrast evolution of an object to a temperature contrast evolution, for modeling afterglow flux, and for assessing the test object emissivity, in accordance with some embodiments described herein. Processing begins at step 1800 whereupon, at block 1805, a steady state temperature measurement is made of the tape affixed to the test object before the flash or the application of heat. At block 1810, the transient thermography IR digital video data of the object, foil, and tape is collected. The collection of data begins before the application of heat. At block 1815, the pixel intensity evolutions at the measurement, reference, tape, and foil ROIs are measured. At block 1820, the normalized pixel intensity (image) contrast evolution is computed using equation (20). At block 1825, the camera constant is computed using equation (65) and the reflection temperature evolution is computed using equation (37). At block 1830, the measurement temperature evolution is computed using equation (55a) and the reference temperature evolution is computed using equation (57). At block 1835, the normalized temperature contrast evolution is computed using equation (23) or equation (51). At block 1840, the afterglow flux is modeled using equation (81). At block 1845, the test object emissivity is assessed using equation (80). Processing subsequently ends at step 1899.

Figure 19:
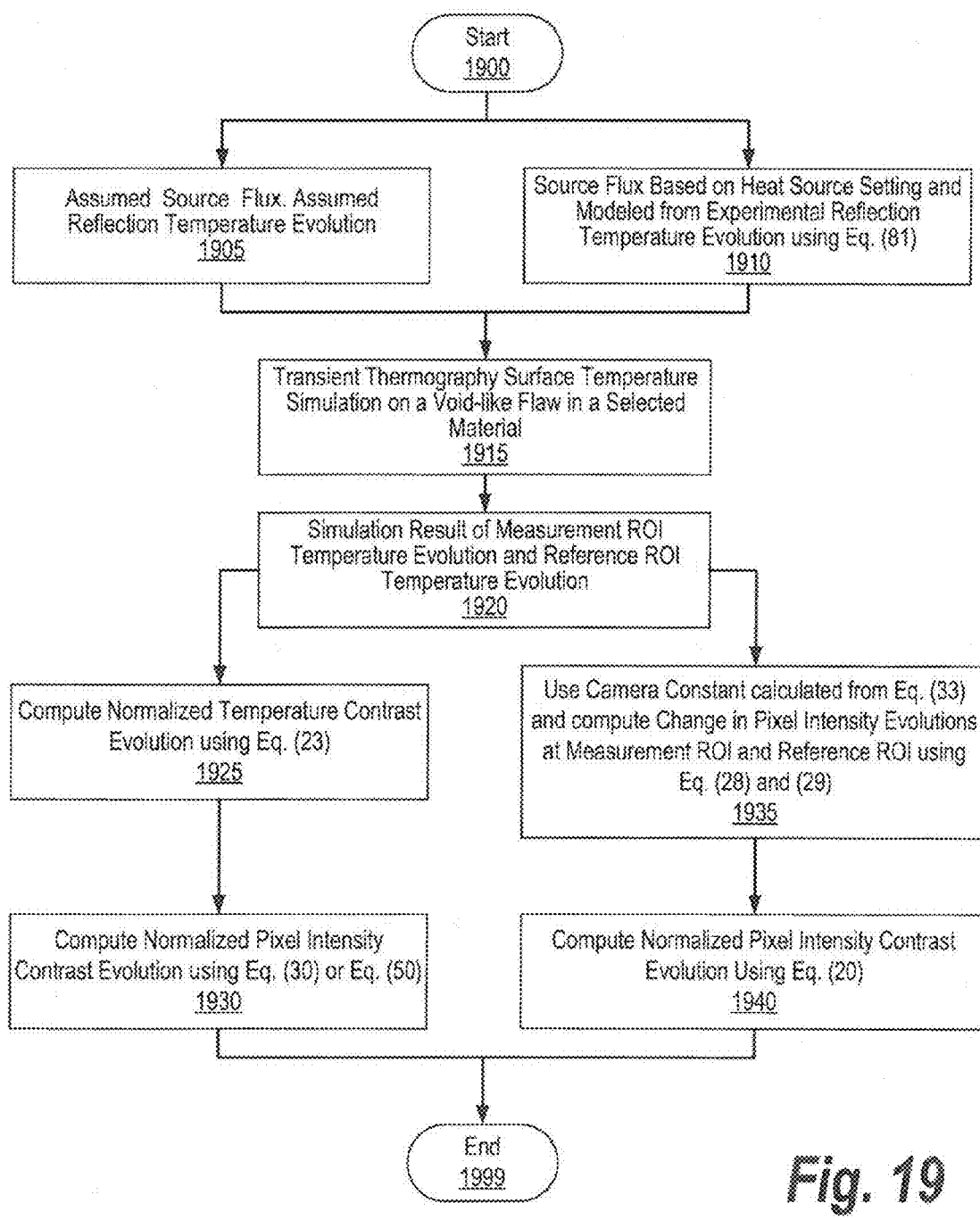
FIG. 19 is a flow diagram illustrating, a method for converting a temperature contrast evolution of an object to an image contrast evolution, in accordance with some embodiments.

FIG. 19 is a flow diagram illustrating a method for converting a temperature contrast evolution of an object to an image contrast evolution, in accordance with some embodiments. Processing begins at step 1900 whereupon either, at block 1905, the source flux and the reflection temperature evolution are assumed, or at block 1910, the source flux is based on the heat source setting and modeled from the experimental reflection temperature evolution using equation (81). At block 1915, the transient thermography surface temperature on a void-like flaw in a selected material is simulated. At block 1920, the measurement ROI temperature evolution and the reference ROI temperature evolution are simulated. At block 1925, the normalized temperature contrast evolution is computed using equation (23), followed by block 1930 where the normalized pixel intensity contrast evolution is computed using equation (30) or equation (50). Alternatively, at block 1935, the camera constant is calculated from equation (33) and the change in pixel intensity evolution at the measurement ROI and the reference ROI are computed using equation (28) and equation (29), respectively, followed by block 1940 where the normalized pixel intensity contrast evolution is computed using equation (20). Processing subsequently ends at, step 1999.

The normalized image contrast and the normalized temperature contrast differ for objects with emissivity other than one. Therefore, for accurate results, the embodiments and examples described herein indicate that the two quantities should not be treated as the same. To compare the simulation temperature contrast with the measured pixel contrast, the method of the embodiments described herein should estimate the evolution of the reflection temperature and the incident heat flux. Ideally, the set of instructions from a computer software program that implements the methods described herein should model the compound heat source flux evolution, which also includes the thermal afterglow. The effect of the reflection temperature on, the pixel intensity should also be accounted for to seek a better estimation of the temperature contrast evolution from the pixel intensity evolution data.

As described herein, the reflection temperature evolution is established based on data acquired by the IRFT data acquisition system. This system acquires readings from a test object, a high emissivity tape with known emissivity, and a diffuse highly reflective metal foil with known reflectivity. The method also records the steady state pre-flash temperature of the object using a thermocouple (or other contact sensor) or an accurate radiometer. The IR datacube is recorded using the normal IRFT technique.

The method comprises four regions of interests (ROIs). One region is for the measurement ROI. The second region is for the reference ROI. The third region is the foil ROI for measurement of the reflection temperature. The fourth region is for measurement of the pre-flash temperature at the high emissivity tape.

Using formulas described previously herein, the method estimates the reflection temperature evolution. The method then computes the temperature contrast from the IRFT data. In accordance with at least one embodiment described herein, the pixel intensity/temperature contrast ratio has been defined in order to relate the temperature contrast to the image contrast.

The embodiments described herein also include a method for using the evolution of the reflection temperature to model the afterglow flux of the flash source. Using the estimated compound source evolution in simulation software, the temperature contrast evolution may be estimated and then the image contrast profiles on the simulated voids may be estimated.

The embodiments described herein include an emissivity estimation technique using the same IR camera that is used in an IRFT system. This method provides determination of the emissivity for the desired thermal wavelength. By using the foil-tape technique during the IRFT shot, the transient reflection temperature or the reflection temperature evolution can be recorded. If an IR camera is programmed with the representative formulas for reflection temperature formulas described herein, the camera can provide the object surface temperature directly, even during the IRFT data acquisition. The IR camera can also be programmed to estimate the object emissivity in real-time by using the formulas described herein in combination with the set-up described for the foil-tape technique.

In light of the principles and exemplary embodiments described and illustrated herein, it will be recognized that the exemplary embodiments can be modified in arrangement and detail without departing from such principles. Also, the foregoing discussion has focused on particular embodiments, but other configurations are contemplated, in particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments.

Similarly, although exemplary processes have been described with regard to particular operations performed in a particular sequence, numerous modifications could be applied to those processes to derive numerous alternative embodiments of those described herein. For example, alternative embodiments may include processes that use fewer than all of the disclosed operations, processes that use additional operations, and processes in which the individual operations disclosed herein are combined, subdivided, rearranged, or otherwise altered.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations. In the claims, means-plus-function and step-plus-function clauses are intended to cover the structures or acts described herein as performing the recited function and not only structural equivalents, but also equivalent structures. Thus, while a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. A method for converting an image contrast evolution of an object to a temperature contrast evolution, the method comprising:

calculating a measurement region of interest temperature change $\Delta T$;

calculating a reference region of interest temperature change $\Delta T$;

calculating a reflection temperature change $\Delta T_{ref}$;

calculating the image contrast evolution $\overline{C}_W^t$; and converting, using a processor, the image contrast evolution $\overline{C}_W^t$ to the temperature contrast evolution $\underline{\overline{C}}^t$ according to the equation of $$\overline{C}^t \cong \left[1 + \frac{2\left(\frac{1}{\varepsilon}-1\right)\Delta T_{refl}}{(\Delta T + \Delta T_{ref})}\right]\overline{C}_W^t$$

wherein $\varepsilon$ is the emissivity of the object.

2. The method of claim 1, where calculating the image contrast evolution comprises:

measuring a measurement region of interest temperature T;

measuring a reference region of interest temperature $T_{ref}$;

measuring a reflection temperature $T_{refl}$; and calculating the image contrast evolution according to the equation of:

$$\overline{C}_W^t \cong \frac{\varepsilon\left((T^4 - T^{0^4}) - (T_{ref}^4 - T_{ref}^{0^4})\right)}{\left(\varepsilon\left((T^4 - T^{0^4}) + (T_{ref}^4 - T_{ref}^{0^4})\right) + 2(1-\varepsilon)(T_{refl}^4 - T_{refl}^{0^4})\right)},$$

wherein $\varepsilon$ is the emissivity of the object, $T^0$ is the measurement region of interest temperature at time of flash, $T_{ref}^0$ is the reference region of interest temperature at time of flash, and $T_{refl}^0$ is the reflection temperature at time of flash.

3. The method of claim 1, where calculating the image contrast evolution comprises:

measuring a measurement region of interest temperature T;

measuring a reference region of interest temperature $T_{ref}$;

measuring a reflection pixel intensity $W_{foil}$;

calculating a camera constant $C'_{cam}$; and calculating the image contrast according to the equation of:

$$\overline{C}_W^t \cong \frac{\varepsilon\left((T^4 - T^{0^4}) - (T_{ref}^4 - T_{ref}^{0^4})\right)}{\varepsilon\left((T^4 - T^{0^4}) + (T_{ref}^4 - T_{ref}^{0^4})\right) + 2\frac{(1-\varepsilon)(W_{foil} - W_{foil}^0)}{C_{cam}(1-\varepsilon_{foil})}}$$

wherein $\varepsilon$ is the emissivity of the object, $\varepsilon_{foil}$ is the emissivity of a foil, $T^0$ is the measurement region of interest temperature at time of flash, $T_{ref}^0$ is the reference region of interest temperature at time of flash, and $W_{foil}^0$ is the reflection region of interest pixel intensity at time of flash.

4. The method of claim 3, where the camera constant is calculated according to the equation of:

$$C'_{cam} = \frac{\left(\frac{W_{tape}^0}{(1-\varepsilon_{tape})} - \frac{W_{foil}^0}{(1-\varepsilon_{foil})}\right)}{\left(\frac{\varepsilon_{tape}}{(1-\varepsilon_{tape})} - \frac{\varepsilon_{foil}}{(1-\varepsilon_{foil})}\right)} \frac{1}{T_{tape}^{0^4}}$$

wherein $\varepsilon_{tape}$ is the emissivity of the tape, $T_{tape}^0$ is the tape region of interest temperature at time of flash, and $W_{tape}^0$ is the tape region of interest pixel intensity at time of flash.

5. A method for assessing an object emissivity, the method comprising:
- measuring a pre-flash temperature at a measurement region of interest $W^0$;
- calculating a camera constant $C'_{cam}$; and
- calculating the object emissivity according to the equation of:

$$\varepsilon \cong \frac{\frac{W^0}{B} - J}{1 - J}$$

wherein $$J = \frac{\left(\frac{W^0_{tape}}{\varepsilon_{tape}} - \frac{W^0_{foil}}{\varepsilon_{foil}}\right)}{\left(\frac{W^0_{tape}}{(1-\varepsilon_{tape})} - \frac{W^0_{foil}}{(1-\varepsilon_{foil})}\right)\left(-\frac{(1-\varepsilon_{tape})}{\varepsilon_{tape}}\frac{(1-\varepsilon_{foil})}{\varepsilon_{foil}}\right)}$$

and $$B = C'_{cam} T^{0^4}_{tape},$$

wherein $\epsilon_{foil}$ is the emissivity of the foil, $\epsilon_{tape}$ is the emissivity of the tape, $T_{tape}^{0}$ is the tape region of interest temperature at time of flash, $W_{foil}^{0}$ is the reflection region of interest pixel intensity at time of flash, and $W_{tape}^{0}$ is the tape region of interest pixel intensity at time of flash.

6. The method of claim 5, where the camera constant is calculated according to the equation of:

$$C'_{cam} \frac{\left(\frac{W^0_{tape}}{(1-\varepsilon_{tape})} - \frac{W^0_{foil}}{(1-\varepsilon_{foil})}\right)}{\left(\frac{\varepsilon_{tape}}{(1-\varepsilon_{tape})} - \frac{\varepsilon_{foil}}{(1-\varepsilon_{foil})}\right)} \frac{1}{T^4_{tape}}.$$

7. A method for calculating an afterglow heat flux evolution, the method comprising:
- measuring a reflection temperature $T_{refl}$, and
- calculating the afterglow heat flux evolution $S_{postflash}$ according to the equation of:

$$S_{postflash} = \sigma(T_{refl}^4 - T_{refl}^{0^4}),$$

wherein $T_{refl}^{0}$ the reflection temperature at time of flash and $\sigma$ is the Stefan-Boltzmann Constant.

* * * * *